United States Patent
Datema et al.

(10) Patent No.: US 11,897,167 B2
(45) Date of Patent: *Feb. 13, 2024

(54) CONCRETE SENSOR SYSTEM

(71) Applicant: Oshkosh Corporation, Oshkosh, WI (US)

(72) Inventors: Bryan S. Datema, Rochester, MN (US); Cody D. Clifton, Oshkosh, WI (US); Jarrod M. Vagle, Oshkosh, WI (US); Xiang Gong, Oshkosh, WI (US); Zhenyi Wei, Oshkosh, WI (US)

(73) Assignee: Oshkosh Corporation, Oshkosh, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,899

(22) Filed: Dec. 5, 2022

(65) Prior Publication Data

US 2023/0116344 A1 Apr. 13, 2023

Related U.S. Application Data

(63) Continuation of application No. 16/743,784, filed on Jan. 15, 2020, now abandoned.
(Continued)

(51) Int. Cl.
*B28C 5/42* (2006.01)
*G01N 33/38* (2006.01)
(Continued)

(52) U.S. Cl.
CPC ............ *B28C 5/422* (2013.01); *B28C 5/4234* (2013.01); *B28C 7/024* (2013.01); *B28C 7/026* (2013.01);
(Continued)

(58) Field of Classification Search
CPC ..... B28C 5/422; B28C 5/4234; B28C 5/4213; G01N 33/383; G01P 1/023; G01P 3/44; G01P 15/02
See application file for complete search history.

(56) References Cited

U.S. PATENT DOCUMENTS 4,114,193 A 9/1978 Hudelmaier
5,752,768 A 5/1998 Assh
(Continued)

FOREIGN PATENT DOCUMENTS

CA 2725887 12/2009
CA 2896786 7/2014
(Continued)

OTHER PUBLICATIONS

U.S. Appl. No. 14/441,412, filed May 7, 2015, Beaupre et al.
(Continued)

*Primary Examiner* — Helen C Kwok
(74) *Attorney, Agent, or Firm* — Foley & Lardner LLP

(57) ABSTRACT

A mixer vehicle includes a mixer drum, a first acceleration sensor, a second acceleration sensor, and a controller. The first acceleration sensor is configured to produce first acceleration signals and the second acceleration sensor is configured to measure accelerations within the mixer drum to produce second acceleration signals. The controller is configured to receive the first acceleration signals from the first acceleration sensor and second acceleration signals from the second acceleration sensor. The controller is further configured to determine a presence of material within the mixer drum based on the first acceleration signals and the second acceleration signals. The controller is further configured to determine one or more properties of the material within the mixer drum based on the first acceleration signals and the second acceleration signals.

20 Claims, 20 Drawing Sheets

Related U.S. Application Data

(60) Provisional application No. 62/793,680, filed on Jan. 17, 2019.

(51) Int. Cl.
 *G01P 3/44* (2006.01)
 *G01P 1/02* (2006.01)
 *G01P 15/02* (2013.01)
 *B28C 7/02* (2006.01)

(52) U.S. Cl.
 CPC ........... *B28C 7/028* (2013.01); *G01N 33/383* (2013.01); *G01P 1/023* (2013.01); *G01P 3/44* (2013.01); *G01P 15/02* (2013.01); *B28C 5/4272* (2013.01)

(56) References Cited

U.S. PATENT DOCUMENTS

| | | | |
|---|---|---|---|
| 5,948,970 A | 9/1999 | Te'eni | |
| 6,484,079 B2 | 11/2002 | Buckelew et al. | |
| 7,578,379 B2 | 8/2009 | Gillmore et al. | |
| 7,648,015 B2 | 1/2010 | Gillmore et al. | |
| 7,931,397 B2 | 4/2011 | Lindblom et al. | |
| 8,287,173 B2 | 10/2012 | Khouri | |
| 8,613,543 B2 | 12/2013 | Lindblom et al. | |
| 8,646,965 B2 | 2/2014 | Datema et al. | |
| 8,727,604 B2 | 5/2014 | Compton et al. | |
| 8,858,061 B2 | 10/2014 | Berman | |
| D737,866 S | 9/2015 | Datema et al. | |
| 9,199,391 B2 | 12/2015 | Beaupre et al. | |
| D772,306 S | 11/2016 | Datema et al. | |
| 9,694,671 B2 | 7/2017 | Wildgrube et al. | |
| 9,952,246 B2 | 4/2018 | Jordan et al. | |
| 10,156,547 B2 | 12/2018 | Biesak et al. | |
| 10,239,403 B2 | 3/2019 | Broker et al. | |
| 10,414,067 B2 | 9/2019 | Datema et al. | |
| 10,792,613 B1 | 10/2020 | Drake et al. | |
| 10,843,379 B2 | 11/2020 | Rocholl et al. | |
| 10,901,409 B2 | 1/2021 | Datema et al. | |
| 11,273,575 B2 | 3/2022 | Roberts et al. | |
| 11,385,153 B2 | 7/2022 | Roberts et al. | |
| 2008/0205188 A1 | 8/2008 | Lindblom et al. | |
| 2009/0050438 A1 | 2/2009 | Gillmore et al. | |
| 2009/0050439 A1 | 2/2009 | Gillmore et al. | |
| 2009/0154287 A1 | 6/2009 | Lindblom et al. | |
| 2009/0171595 A1 | 7/2009 | Bonilla Benegas | |
| 2011/0058446 A1 | 3/2011 | Khouri | |
| 2013/0107656 A1 | 5/2013 | Datema et al. | |
| 2015/0078417 A1 | 3/2015 | Verdino | |
| 2015/0159564 A1 | 6/2015 | Wildgrube et al. | |
| 2015/0246331 A1 | 9/2015 | Broker et al. | |
| 2015/0355160 A1* | 12/2015 | Berman | G01N 27/048 |
| | | | 73/54.03 |
| 2016/0018383 A1 | 1/2016 | Radjy | |
| 2017/0108421 A1 | 4/2017 | Beaupre et al. | |
| 2017/0297425 A1 | 10/2017 | Wildgrube et al. | |
| 2017/0361491 A1 | 12/2017 | Datema et al. | |
| 2017/0361492 A1 | 12/2017 | Datema et al. | |
| 2017/0370898 A1 | 12/2017 | Radjy et al. | |
| 2018/0250847 A1 | 9/2018 | Wurtz et al. | |
| 2019/0091890 A1 | 3/2019 | Rocholl et al. | |
| 2019/0121353 A1 | 4/2019 | Datema et al. | |
| 2019/0217698 A1 | 7/2019 | Broker et al. | |
| 2019/0325220 A1 | 10/2019 | Wildgrube et al. | |
| 2019/0344475 A1 | 11/2019 | Datema et al. | |
| 2020/0078986 A1 | 3/2020 | Clifton et al. | |
| 2020/0094671 A1 | 3/2020 | Wildgrube et al. | |
| 2020/0217833 A1* | 7/2020 | Davis | G01N 29/245 |
| 2020/0230841 A1 | 7/2020 | Datema et al. | |
| 2020/0230842 A1 | 7/2020 | Datema et al. | |
| 2020/0289985 A1 | 9/2020 | Drake et al. | |
| 2021/0001765 A1* | 1/2021 | Beaupre | B28C 5/422 |
| 2021/0031649 A1 | 2/2021 | Messina et al. | |
| 2021/0039719 A1 | 2/2021 | Datema et al. | |
| 2021/0237311 A1* | 8/2021 | Datema | B28C 5/4234 |

FOREIGN PATENT DOCUMENTS

| | | |
|---|---|---|
| EP | 2 977 163 A1 | 1/2016 |
| ES | 2281267 A1 | 9/2007 |
| JP | 2004-154996 A | 6/2004 |
| JP | 2014-004769 A | 1/2014 |
| WO | WO-2009/144523 A2 | 12/2009 |
| WO | WO-2014/108798 | 7/2014 |

OTHER PUBLICATIONS

U.S. Appl. No. 14/472,452, filed Aug. 29, 2014, Katzeff-Berman Dully [IL].

U.S. Appl. No. 14/760,269, filed Jul. 10, 2015, Katzeff-Berman Dully [IL/CA].

U.S. Appl. No. 14/775,373, filed Sep. 11, 2015, Beaupre et al.

U.S. Appl. No. 61/751,663.

Luu L, Dinh A. "Artifact Noise Removal Techniques on Seismocardiogram Using Two Tri-Axial Accelerometers". Sensors (Basel). Apr. 2, 2018; 18(4):1067. (Year: 2018).

\* cited by examiner

CONCRETE SENSOR SYSTEM

CROSS-REFERENCE TO RELATED PATENT APPLICATION

This application is a continuation of U.S. application Ser. No. 16/743,784, filed Jan. 15, 2020, which claims the benefit of and priority to U.S. Provisional Patent Application No. 62/793,680, filed Jan. 17, 2019, which is incorporated herein by reference in its entirety.

BACKGROUND

Concrete mixer vehicles are configured to receive, mix, and transport wet concrete or a combination of ingredients that when mixed form wet concrete to a job site. Concrete mixer vehicles include a rotatable mixer drum that mixes the concrete disposed therein.

SUMMARY

One implementation of the present disclosure is a mixer vehicle including a mixer drum, a first acceleration sensor, a second acceleration sensor, and a controller, according to an exemplary embodiment. The first acceleration sensor is configured to produce first acceleration signals and the second acceleration sensor is configured to measure accelerations within the mixer drum to produce second acceleration signals. The controller is configured to receive the first acceleration signals from the first acceleration sensor and second acceleration signals from the second acceleration sensor. The controller is further configured to determine a presence of material within the mixer drum based on the first acceleration signals and the second acceleration signals. The controller is further configured to determine one or more properties of the material within the mixer drum based on the first acceleration signals and the second acceleration signals.

Another implementation of the present disclosure is a sensing system for a concrete mixer vehicle, according to an exemplary embodiment. The sensing system includes a controller having a processing circuit configured to receive first acceleration signals from a first acceleration sensor and second acceleration signals from a second acceleration sensor. The second acceleration sensor is positioned within a mixer drum of the concrete mixer vehicle to produce the second acceleration signals. The processing circuit is further configured to determine a presence of material within the mixer drum based on the first acceleration signals and the second acceleration signals. The processing circuit is further configured to determine one or more properties of the material within the mixer drum based on the first acceleration signals and the second acceleration signals.

Another implementation of the present disclosure is a method for determining a slump of a material within a concrete mixer drum, according to an exemplary embodiment. The method includes providing a first acceleration sensor and a second acceleration sensor. The first acceleration sensor is configured to produce baseline acceleration signals as the concrete mixer drum rotates, and the second acceleration sensor is configured to produce disturbed or noisy acceleration signals as the concrete mixer drum rotates. The method includes obtaining the baseline acceleration signals and the disturbed or noisy acceleration signals as the concrete mixer drum rotates. The method includes comparing the baseline acceleration signals and the disturbed or noisy acceleration signals to each other to identify an amount of noise in the disturbed acceleration signals. The method includes using the amount of noise in the disturbed acceleration signals to estimate the slump of the material within the concrete mixer drum.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Figure 1:
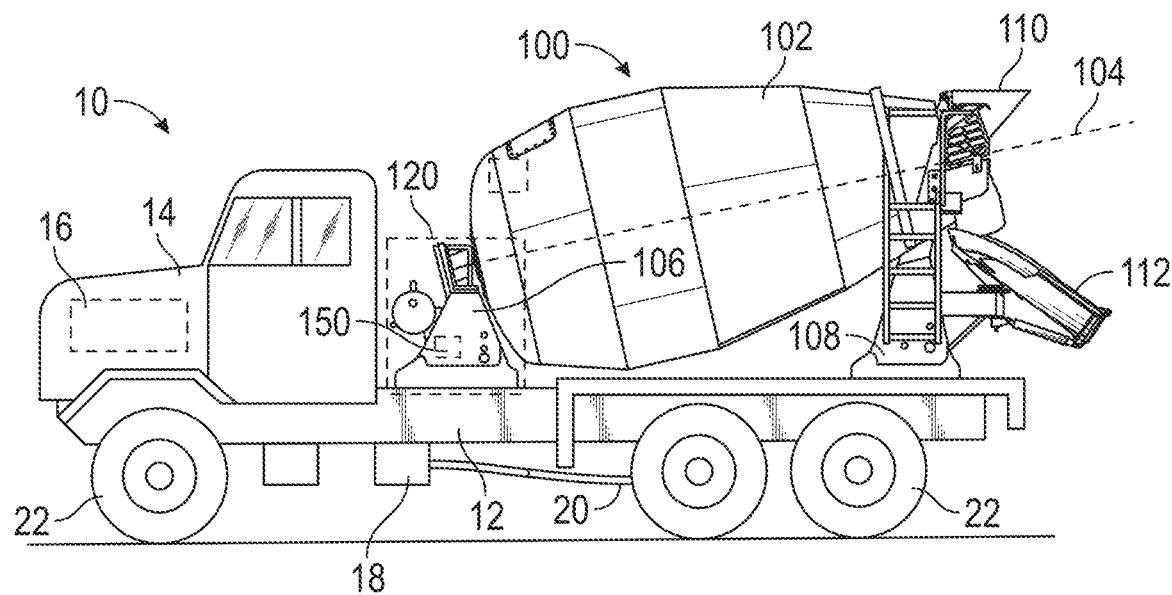
FIG. 1 is a side view of a concrete mixer truck with a drum assembly and a control system, according to an exemplary embodiment.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring generally to the FIGURES, a concrete sensor system for a concrete mixing vehicle having a mixer drum is shown, according to an exemplary embodiment. The concrete sensor system includes a sensor assembly (e.g., a probe) including a first accelerometer and a second accelerometer. The first accelerometer is positioned such that it measures a baseline acceleration signal. For example, the first accelerometer may be positioned outside of the mixer drum, inside the mixer drum in an enclosure, within a housing of the probe, etc. The second accelerometer is positioned such that it passes through mixture present in the mixer drum and measures acceleration signals which are disturbed due to the second accelerometer passing through the mixture. The first accelerometer and the second accelerometer may be three-axis accelerometers, configured to measure radial, tangential, and lateral acceleration. As the mixer drum rotates, the measured radial and tangential acceleration changes according to a sinusoidal shape due to the changing amounts of gravitational acceleration measured in the radial and tangential directions. As the mixer drum rotates and the second accelerometer passes through mixture which may be present in the mixer drum, the second accelerometer produces disturbed/noisy acceleration signals. Since the first accelerometer is outside of the mixer drum or positioned such that it does not pass through the mixture, the first accelerometer produces undisturbed/baseline acceleration signals. In some embodiments, the first accelerometer and the second accelerometer are used to determine a difference. In some embodiments, the difference is a difference between the measured acceleration signals of the first and second accelerometers, a difference between one of the first and second accelerometers and a firm object (e.g., the mixer drum), etc. A controller can analyze the disturbed acceleration signals and the undisturbed acceleration signals, and based on the analysis of the disturbed/undisturbed acceleration signals can determine any of whether material is present in the mixer drum, material properties (e.g., slump) of the material/mixture present in the mixer drum, quantity of material/mixture present in the mixer drum, entry/exit angles of material/mixture present in the mixer drum, mixer drum orientation, mixer drum speed, number of revolutions of the mixer drum, etc., according to an exemplary embodiment. Additionally, the controller can use the undisturbed acceleration signals to filter out external accelerations of the disturbed acceleration signals. The determined amount of material/mixture present in the mixer drum can be validated using a concrete buildup algorithm. The sensor assembly/probe may be coated with a urethane covering, removing the potential for material/mixture such as concrete to build up on the second accelerometer. The calculated weight can be used for a variety of applications such as automating BM axle pressure. Knowing the orientation of the mixer drum facilitates automatically adjusting an orientation of the mixer drum. This may be advantageously used to adjust the orientation of the mixer drum such that a solar panel faces upwards or towards the sun, or so that a hatch of the mixer drum is near a fender for charging purposes. Additionally, after mixture/concrete/material has been delivered to a receiving site/area, the orientation of the mixer drum may be adjusted (e.g., rotated) such that the probe is not within any potential leftover concrete. Rotating the probe out of the leftover concrete may facilitate keeping the probe clean and safe from damage. Additionally, the sensor assembly can be removably attached to the mixer drum and the controller, facilitating easy removal, replacement, cleaning, etc. The sensor system described herein is an inexpensive system which reduces the need for expensive weighing systems.

According to the exemplary embodiment shown in FIGS. 1-5, a vehicle, shown as concrete mixer truck 10, includes a drum assembly, shown as drum assembly 100, and a control system, shown as drum control system 150. According to an exemplary embodiment, the concrete mixer truck 10 is configured as a rear-discharge concrete mixer truck. In other embodiments, the concrete mixer truck 10 is configured as a front-discharge concrete mixer truck. As shown in FIG. 1, the concrete mixer truck 10 includes a chassis, shown as frame 12, and a cab, shown as cab 14, coupled to the frame 12 (e.g., at a front end thereof, etc.). The drum assembly 100 is coupled to the frame 12 and disposed behind the cab 14 (e.g., at a rear end thereof, etc.), according to the exemplary embodiment shown in FIG. 1. In other embodiments, at least a portion of the drum assembly 100 extends in front of the cab 14. The cab 14 may include various components to facilitate operation of the concrete mixer truck 10 by an operator (e.g., a seat, a steering wheel, hydraulic controls, a user interface, switches, buttons, dials, etc.).

Figure 3:
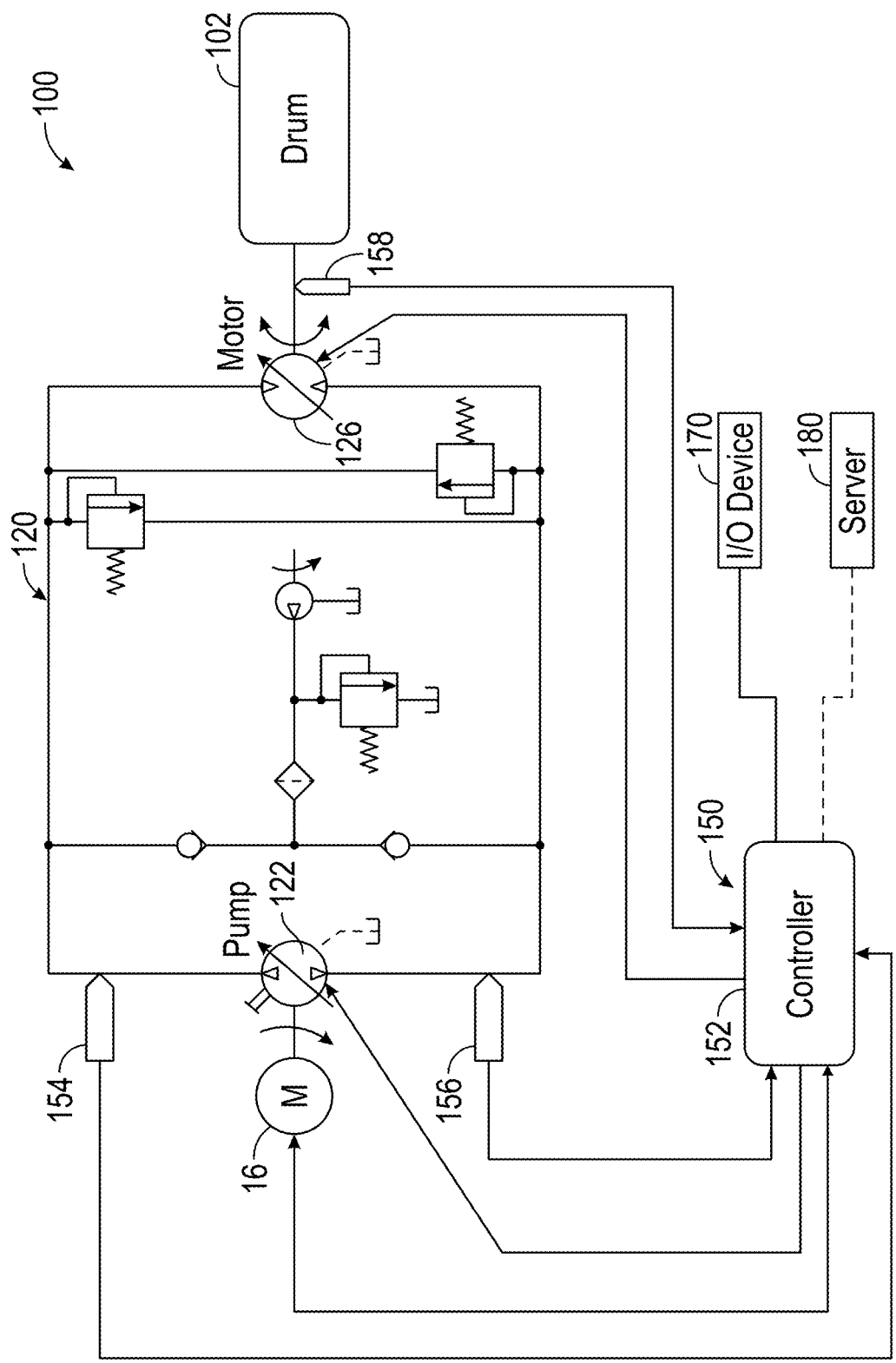
FIG. 3 is a schematic diagram of a drum drive system of the concrete mixer truck of FIG. 1, according to an exemplary embodiment.
Figure 4:
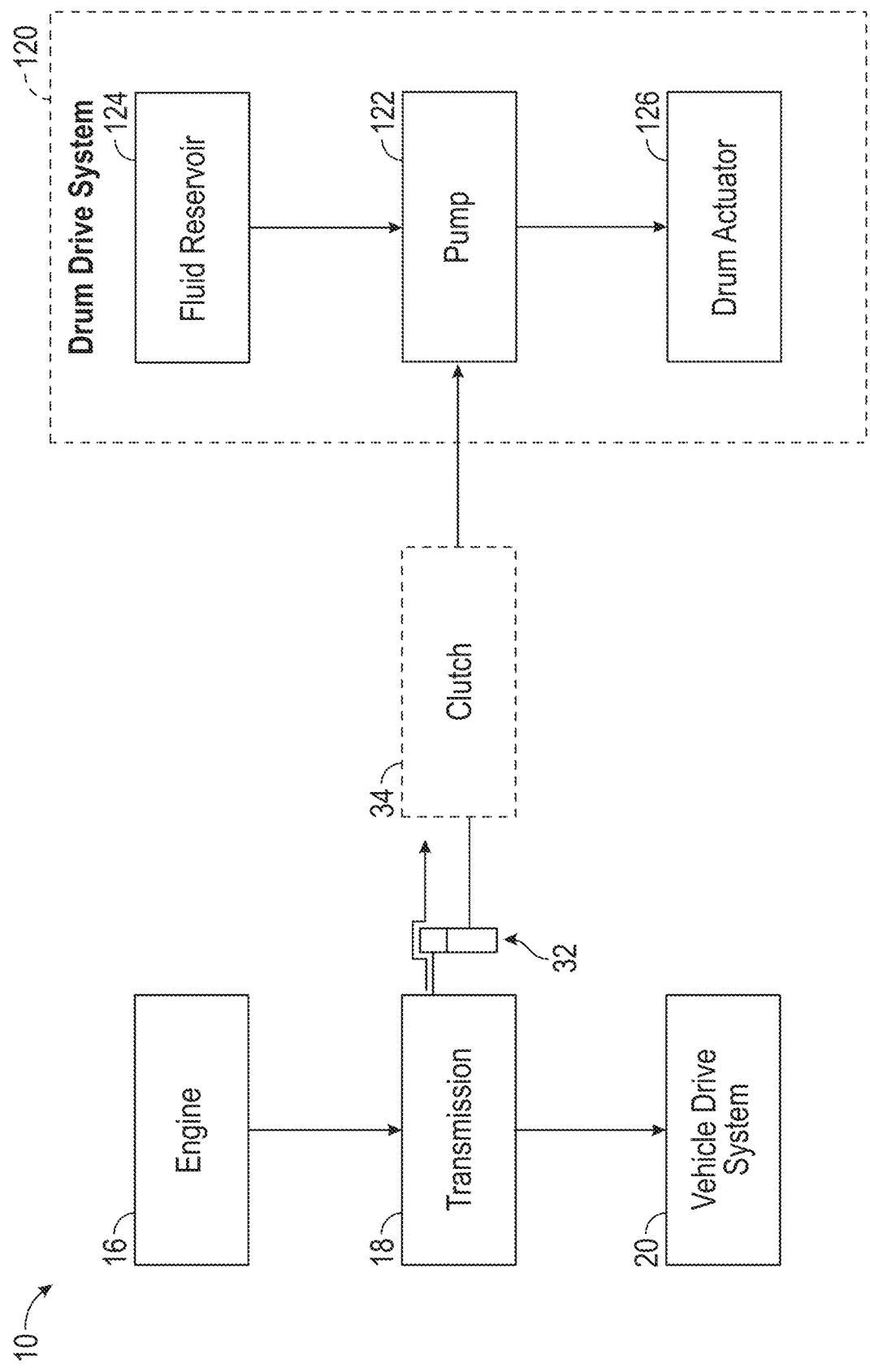
FIG. 4 is a power flow diagram for the concrete mixer truck of FIG. 1 having a drum drive system that is selectively coupled to a transmission with a clutch, according to an exemplary embodiment.
Figure 5:
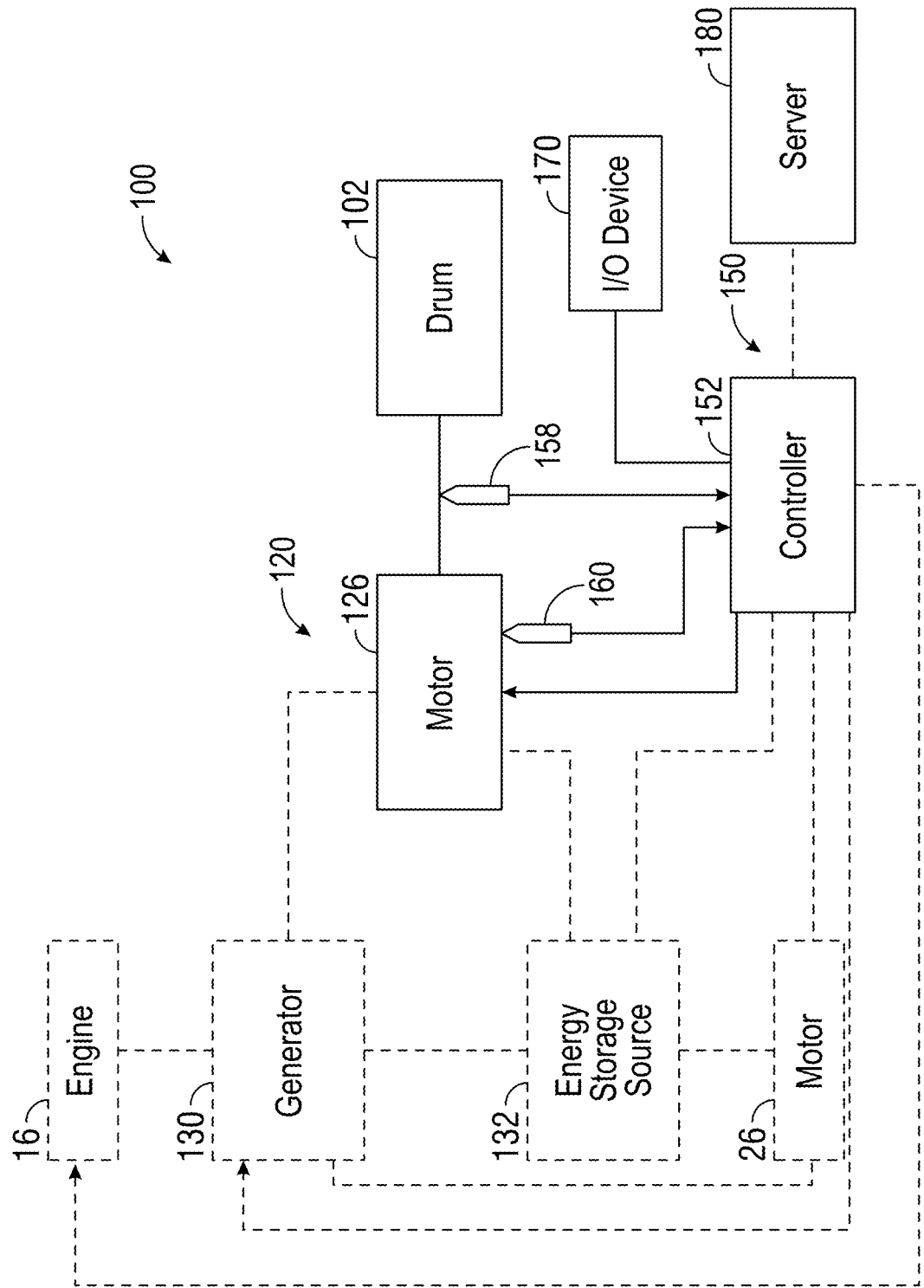
FIG. 5 is a schematic diagram of a drum drive system of the concrete mixer truck of FIG. 1, according to another exemplary embodiment.

As shown in FIGS. 1, 3, and 4, the concrete mixer truck 10 includes a prime mover, shown as engine 16. As shown in FIG. 1, the engine 16 is coupled to the frame 12 at a position beneath the cab 14. The engine 16 may be configured to utilize one or more of a variety of fuels (e.g., gasoline, diesel, bio-diesel, ethanol, natural gas, etc.), according to various exemplary embodiments. According to an alternative embodiment, as shown in FIG. 5 and described in more detail herein, the prime mover additionally or alternatively includes one or more electric motors and/or generators, which may be coupled to the frame 12 (e.g., a hybrid vehicle, an electric vehicle, etc.). The electric motors may consume electrical power from an on-board storage device (e.g., batteries, ultra-capacitors, etc.), from an on-board generator (e.g., an internal combustion engine, a genset, etc.), and/or from an external power source (e.g., overhead power lines, etc.) and provide power to systems of the concrete mixer truck 10.

As shown in FIGS. 1 and 4, the concrete mixer truck 10 includes a power transfer device, shown as transmission 18. In one embodiment, the engine 16 produces mechanical power (e.g., due to a combustion reaction, etc.) that flows into the transmission 18. As shown in FIGS. 1 and 4, the concrete mixer truck 10 includes a first drive system, shown as vehicle drive system 20, that is coupled to the transmission 18. The vehicle drive system 20 may include drive shafts, differentials, and other components coupling the transmission 18 with a ground surface to move the concrete mixer truck 10. As shown in FIG. 1, the concrete mixer truck 10 includes a plurality of tractive elements, shown as wheels 22, that engage a ground surface to move the concrete mixer truck 10. In one embodiment, at least a portion of the mechanical power produced by the engine 16 flows through the transmission 18 and into the vehicle drive system 20 to power at least a portion of the wheels 22 (e.g., front wheels, rear wheels, etc.). In one embodiment, energy (e.g., mechanical energy, etc.) flows along a first power path defined from the engine 16, through the transmission 18, and to the vehicle drive system 20.

Figure 2:
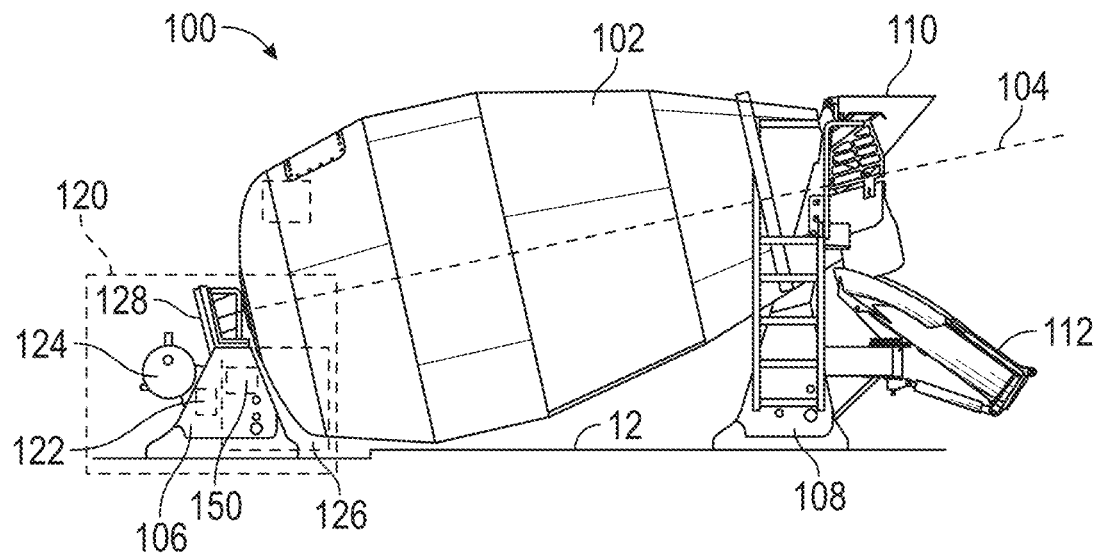
FIG. 2 is a detailed side view of the drum assembly of the concrete mixer truck of FIG. 1, according to an exemplary embodiment.

As shown in FIGS. 1-3 and 5, the drum assembly 100 of the concrete mixer truck 10 includes a drum, shown as mixer drum 102. The mixer drum 102 is coupled to the frame 12 and disposed behind the cab 14 (e.g., at a rear and/or middle of the frame 12, etc.). As shown in FIGS. 1-5, the drum assembly 100 includes a second drive system, shown as drum drive system 120, that is coupled to the frame 12. As shown in FIGS. 1 and 2, the concrete mixer truck 10 includes a first support, shown as front pedestal 106, and a second support, shown as rear pedestal 108. According to an exemplary embodiment, the front pedestal 106 and the rear pedestal 108 cooperatively couple (e.g., attach, secure, etc.) the mixer drum 102 to the frame 12 and facilitate rotation of the mixer drum 102 relative to the frame 12. In an alternative embodiment, the drum assembly 100 is configured as a stand-alone mixer drum that is not coupled (e.g., fixed, attached, etc.) to a vehicle. In such an embodiment, the drum assembly 100 may be mounted to a stand-alone frame. The stand-alone frame may be a chassis including wheels that assist with the positioning of the stand-alone mixer drum on a worksite. Such a stand-alone mixer drum may also be detachably coupled to and/or capable of being loaded onto a vehicle such that the stand-alone mixer drum may be transported by the vehicle.

As shown in FIGS. 1 and 2, the mixer drum 102 defines a central, longitudinal axis, shown as axis 104. According to an exemplary embodiment, the drum drive system 120 is configured to selectively rotate the mixer drum 102 about the axis 104. As shown in FIGS. 1 and 2, the axis 104 is angled relative to the frame 12 such that the axis 104 intersects with the frame 12. According to an exemplary embodiment, the axis 104 is elevated from the frame 12 at an angle in the range of five degrees to twenty degrees. In other embodiments, the axis 104 is elevated by less than five degrees (e.g., four degrees, three degrees, etc.) or greater than twenty degrees (e.g., twenty-five degrees, thirty degrees, etc.). In an alternative embodiment, the concrete mixer truck 10 includes an actuator positioned to facilitate selectively adjusting the axis 104 to a desired or target angle (e.g., manually in response to an operator input/command, automatically according to a control scheme, etc.).

As shown in FIGS. 1 and 2, the mixer drum 102 of the drum assembly 100 includes an inlet, shown as hopper 110, and an outlet, shown as chute 112. According to an exemplary embodiment, the mixer drum 102 is configured to receive a mixture, such as a concrete mixture (e.g., cementitious material, aggregate, sand, etc.), with the hopper 110. The mixer drum 102 may include a mixing element (e.g., fins, etc.) positioned within the interior thereof. The mixing element may be configured to (i) agitate the contents of mixture within the mixer drum 102 when the mixer drum 102 is rotated by the drum drive system 120 in a first direction (e.g., counterclockwise, clockwise, etc.) and (ii) drive the mixture within the mixer drum 102 out through the chute 112 when the mixer drum 102 is rotated by the drum drive system 120 in an opposing second direction (e.g., clockwise, counterclockwise, etc.).

According to the exemplary embodiment shown in FIGS. 2-4, the drum drive system is a hydraulic drum drive system. As shown in FIGS. 2-4, the drum drive system 120 includes a pump, shown as pump 122; a reservoir, shown as fluid reservoir 124, fluidly coupled to the pump 122; and an actuator, shown as drum motor 126. As shown in FIGS. 3 and 4, the pump 122 and the drum motor 126 are fluidly coupled. According to an exemplary embodiment, the drum motor 126 is a hydraulic motor, the fluid reservoir 124 is a hydraulic fluid reservoir, and the pump 122 is a hydraulic pump. The pump 122 may be configured to pump fluid (e.g., hydraulic fluid, etc.) stored within the fluid reservoir 124 to drive the drum motor 126.

According to an exemplary embodiment, the pump 122 is a variable displacement hydraulic pump (e.g., an axial piston pump, etc.) and has a pump stroke that is variable. The pump 122 may be configured to provide hydraulic fluid at a flow rate that varies based on the pump stroke (e.g., the greater the pump stroke, the greater the flow rate provided to the drum motor 126, etc.). The pressure of the hydraulic fluid provided by the pump 122 may also increase in response to an increase in pump stroke (e.g., where pressure may be directly related to work load, higher flow may result in higher pressure, etc.). The pressure of the hydraulic fluid provided by the pump 122 may alternatively not increase in response to an increase in pump stroke (e.g., in instances where there is little or no work load, etc.). The pump 122 may include a throttling element (e.g., a swash plate, etc.). The pump stroke of the pump 122 may vary based on the orientation of the throttling element. In one embodiment, the pump stroke of the pump 122 varies based on an angle of the throttling element (e.g., relative to an axis along which the pistons move within the axial piston pump, etc.). By way of example, the pump stroke may be zero where the angle of the throttling element is equal to zero. The pump stroke may increase as the angle of the throttling element increases. According to an exemplary embodiment, the variable pump stroke of the pump 122 provides a variable speed range of up to about 10:1. In other embodiments, the pump 122 is configured to provide a different speed range (e.g., greater than 10:1, less than 10:1, etc.).

In one embodiment, the throttling element of the pump 122 is movable between a stroked position (e.g., a maximum stroke position, a partially stroked position, etc.) and a destroked position (e.g., a minimum stroke position, a partially destroked position, etc.). According to an exemplary embodiment, an actuator is coupled to the throttling element of the pump 122. The actuator may be positioned to move the throttling element between the stroked position and the destroked position. In some embodiments, the pump 122 is configured to provide no flow, with the throttling element in a non-stroked position, in a default condition (e.g., in response to not receiving a stroke command, etc.). The throttling element may be biased into the non-stroked position. In some embodiments, the drum control system 150 is configured to provide a first command signal. In response to receiving the first command signal, the pump 122 (e.g., the throttling element by the actuator thereof, etc.) may be selectively reconfigured into a first stroke position (e.g., stroke in one direction, a destroked position, etc.). In some embodiments, the drum control system 150 is configured to additionally or alternatively provide a second command signal. In response to receiving the second command signal, the pump 122 (e.g., the throttling element by the actuator thereof, etc.) may be selectively reconfigured into a second stroke position (e.g., stroke in an opposing second direction, a stroked position, etc.). The pump stroke may be related to the position of the throttling element and/or the actuator.

According to another exemplary embodiment, a valve is positioned to facilitate movement of the throttling element between the stroked position and the destroked position. In one embodiment, the valve includes a resilient member (e.g., a spring, etc.) configured to bias the throttling element in the destroked position (e.g., by biasing movable elements of the valve into positions where a hydraulic circuit actuates the throttling element into the destroked positions, etc.). Pressure from fluid flowing through the pump 122 may overcome the resilient member to actuate the throttling element into the stroked position (e.g., by actuating movable elements of the valve into positions where a hydraulic circuit actuates the throttling element into the stroked position, etc.).

As shown in FIG. 4, the concrete mixer truck 10 includes a power takeoff unit, shown as power takeoff unit 32, that is coupled to the transmission 18. In another embodiment, the power takeoff unit 32 is coupled directly to the engine 16. In one embodiment, the transmission 18 and the power takeoff unit 32 include mating gears that are in meshing engagement. A portion of the energy provided to the transmission 18 flows through the mating gears and into the power takeoff unit 32, according to an exemplary embodiment. In one embodiment, the mating gears have the same effective diameter. In other embodiments, at least one of the mating gears has a larger diameter, thereby providing a gear reduction or a torque multiplication and increasing or decreasing the gear speed.

As shown in FIG. 4, the power takeoff unit 32 is selectively coupled to the pump 122 with a clutch 34. In other embodiments, the power takeoff unit 32 is directly coupled to the pump 122 (e.g., without clutch 34, etc.). In some embodiments, the concrete mixer truck 10 does not include the clutch 34. By way of example, the power takeoff unit 32 may be directly coupled to the pump 122 (e.g., a direct configuration, a non-clutched configuration, etc.). According to an alternative embodiment, the power takeoff unit 32 includes the clutch 34 (e.g., a hot shift PTO, etc.). In one embodiment, the clutch 34 includes a plurality of clutch discs. When the clutch 34 is engaged, an actuator forces the plurality of clutch discs into contact with one another, which couples an output of the transmission 18 with the pump 122. In one embodiment, the actuator includes a solenoid that is electronically actuated according to a clutch control strategy. When the clutch 34 is disengaged, the pump 122 is not coupled to (i.e., is isolated from) the output of the transmission 18. Relative movement between the clutch discs or movement between the clutch discs and another component of the power takeoff unit 32 may be used to decouple the pump 122 from the transmission 18.

In one embodiment, energy flows along a second power path defined from the engine 16, through the transmission 18 and the power takeoff unit 32, and into the pump 122 when the clutch 34 is engaged. When the clutch 34 is disengaged, energy flows from the engine 16, through the transmission 18, and into the power takeoff unit 32. The clutch 34 selectively couples the pump 122 to the engine 16, according to an exemplary embodiment. In one embodiment, energy along the first flow path is used to drive the wheels 22 of the concrete mixer truck 10, and energy along the second flow path is used to operate the drum drive system 120 (e.g., power the pump 122, etc.). By way of example, the clutch 34 may be engaged such that energy flows along the second flow path when the pump 122 is used to provide hydraulic fluid to the drum motor 126. When the pump 122 is not used to drive the mixer drum 102 (e.g., when the mixer drum 102 is empty, etc.), the clutch 34 may be selectively disengaged, thereby conserving energy. In embodiments without clutch 34, the mixer drum 102 may continue turning (e.g., at low speed) when empty.

The drum motor 126 is positioned to drive the rotation of the mixer drum 102. In some embodiments, the drum motor 126 is a fixed displacement motor. In some embodiments, the drum motor 126 is a variable displacement motor. In one embodiment, the drum motor 126 operates within a variable speed range up to about 3:1 or 4:1. In other embodiments, the drum motor 126 is configured to provide a different speed range (e.g., greater than 4:1, less than 3:1, etc.). According to an exemplary embodiment, the speed range of the drum drive system 120 is the product of the speed range of the pump 122 and the speed range of the drum motor 126. The drum drive system 120 having a variable pump 122 and a variable drum motor 126 may thereby have a speed range that reaches up to 30:1 or 40:1 (e.g., without having to operate the engine 16 at a high idle condition, etc.). According to an exemplary embodiment, increased speed range of the drum drive system 120 having a variable displacement motor and a variable displacement pump relative to a drum drive system having a fixed displacement motor frees up boundary limits for the engine 16, the pump 122, and the drum motor 126. Advantageously, with the increased capacity of the drum drive system 120, the engine 16 does not have to run at either high idle or low idle during the various operating modes of the drum assembly 100 (e.g., mixing mode, discharging mode, filling mode, etc.), but rather the engine 16 may be operated at a speed that provides the most fuel efficiency and most stable torque. Also, the pump 122 and the drum motor 126 may not have to be operated at displacement extremes to meet the speed requirements for the mixer drum 102 during various applications, but can rather be modulated to the most efficient working conditions (e.g., by the drum control system 150, etc.).

As shown in FIG. 2, the drum drive system 120 includes a drive mechanism, shown as drum drive wheel 128, coupled to the mixer drum 102. The drum drive wheel 128 may be welded, bolted, or otherwise secured to the head of the mixer drum 102. The center of the drum drive wheel 128 may be positioned along the axis 104 such that the drum drive wheel 128 rotates about the axis 104. According to an exemplary embodiment, the drum motor 126 is coupled to the drum drive wheel 128 (e.g., with a belt, a chain, a gearing arrangement, etc.) to facilitate driving the drum drive wheel 128 and thereby rotate the mixer drum 102. The drum drive wheel 128 may be or include a sprocket, a cogged wheel, a grooved wheel, a smooth-sided wheel, a sheave, a pulley, or still another member. In other embodiments, the drum drive system 120 does not include the drum drive wheel 128. By way of example, the drum drive system 120 may include a gearbox that couples the drum motor 126 to the mixer drum 102. By way of another example, the drum motor 126 (e.g., an output thereof, etc.) may be directly coupled to the mixer drum 102 (e.g., along the axis 104, etc.) to rotate the mixer drum 102.

According to the exemplary embodiment shown in FIG. 5, the drum drive system 120 of the drum assembly 100 is configured to be an electric drum drive system. As shown in FIG. 5, the drum drive system 120 includes the drum motor 126, which is electrically powered to drive the mixer drum 102. By way of example, in an embodiment where the concrete mixer truck 10 has a hybrid powertrain, the engine 16 may drive a generator (e.g., with the power takeoff unit 32, etc.), shown as generator 130, to generate electrical power that is (i) stored for future use by the drum motor 126 in storage (e.g., battery cells, etc.), shown as energy storage source 132, and/or (ii) provided directly to drum motor 126 to drive the mixer drum 102. The energy storage source 132 may additionally be chargeable using a mains power connection (e.g., through a charging station, etc.). By way of another example, in an embodiment where the concrete mixer truck 10 has an electric powertrain, the engine 16 may be replaced with a main motor, shown as primary motor 26, that drives the wheels 22. The primary motor 26 and the drum motor 126 may be powered by the energy storage source 132 and/or the generator 130 (e.g., a regenerative braking system, etc.).

According to the exemplary embodiments shown in FIGS. 3 and 5, the drum control system 150 for the drum assembly 100 of the concrete mixer truck 10 includes a controller, shown as drum assembly controller 152. In one embodiment, the drum assembly controller 152 is configured to selectively engage, selectively disengage, control, and/or otherwise communicate with components of the drum assembly 100 and/or the concrete mixer truck 10 (e.g., actively control the components thereof, etc.). As shown in FIGS. 3 and 5, the drum assembly controller 152 is coupled to the engine 16, the primary motor 26, the pump 122, the drum motor 126, the generator 130, the energy storage source 132, a pressure sensor 154, a temperature sensor 156, a speed sensor 158, a motor sensor 160, an input/output ("I/O") device 170, and/or a remote server 180. In other embodiments, the drum assembly controller 152 is coupled to more or fewer components. By way of example, the drum assembly controller 152 may send and/or receive signals with the engine 16, the primary motor 26, the pump 122, the drum motor 126, the generator 130, the energy storage source 132, the pressure sensor 154, the temperature sensor 156, the speed sensor 158, the motor sensor 160, the I/O device 170, and/or the remote server 180.

The drum assembly controller 152 may be implemented as hydraulic controls, a general-purpose processor, an application specific integrated circuit (ASIC), one or more field programmable gate arrays (FPGAs), a digital-signal-processor (DSP), circuits containing one or more processing components, circuitry for supporting a microprocessor, a group of processing components, or other suitable electronic processing components. According to an exemplary embodiment, the drum assembly controller 152 includes a processing circuit having a processor and a memory. The processing circuit may include an ASIC, one or more FPGAs, a DSP, circuits containing one or more processing components, circuitry for supporting a microprocessor, a group of processing components, or other suitable electronic processing components. In some embodiments, the processor is configured to execute computer code stored in the memory to facilitate the activities described herein. The memory may be any volatile or non-volatile computer-readable storage medium capable of storing data or computer code relating to the activities described herein. According to an exemplary embodiment, the memory includes computer code modules (e.g., executable code, object code, source code, script code, machine code, etc.) configured for execution by the processor.

According to an exemplary embodiment, the drum assembly controller 152 is configured to facilitate detecting the buildup of concrete within the mixer drum 102. By way of example, over time after various concrete discharge cycles, concrete may begin to build up and harden within the mixer drum 102. Such buildup is disadvantageous because of the increased weight of the concrete mixer truck 10 and decreased charge capacity of the mixer drum 102. Such factors may reduce the efficiency of concrete delivery. Therefore, the concrete that has built up must be cleaned from the interior of the mixer drum 102 (i.e., using a chipping process). Typically, the buildup is monitored either (i) manually by the operator of the concrete mixer truck 10 (e.g., by inspecting the interior of the mixer drum 102, etc.) or (ii) using expensive load cells to detect a change in mass of the mixer drum 102 when empty. According to an exemplary embodiment, the drum assembly controller 152 is configured to automatically detect concrete buildup within the mixer drum 102 using sensor measurements from more cost effective sensors and processes.

Figure 6:
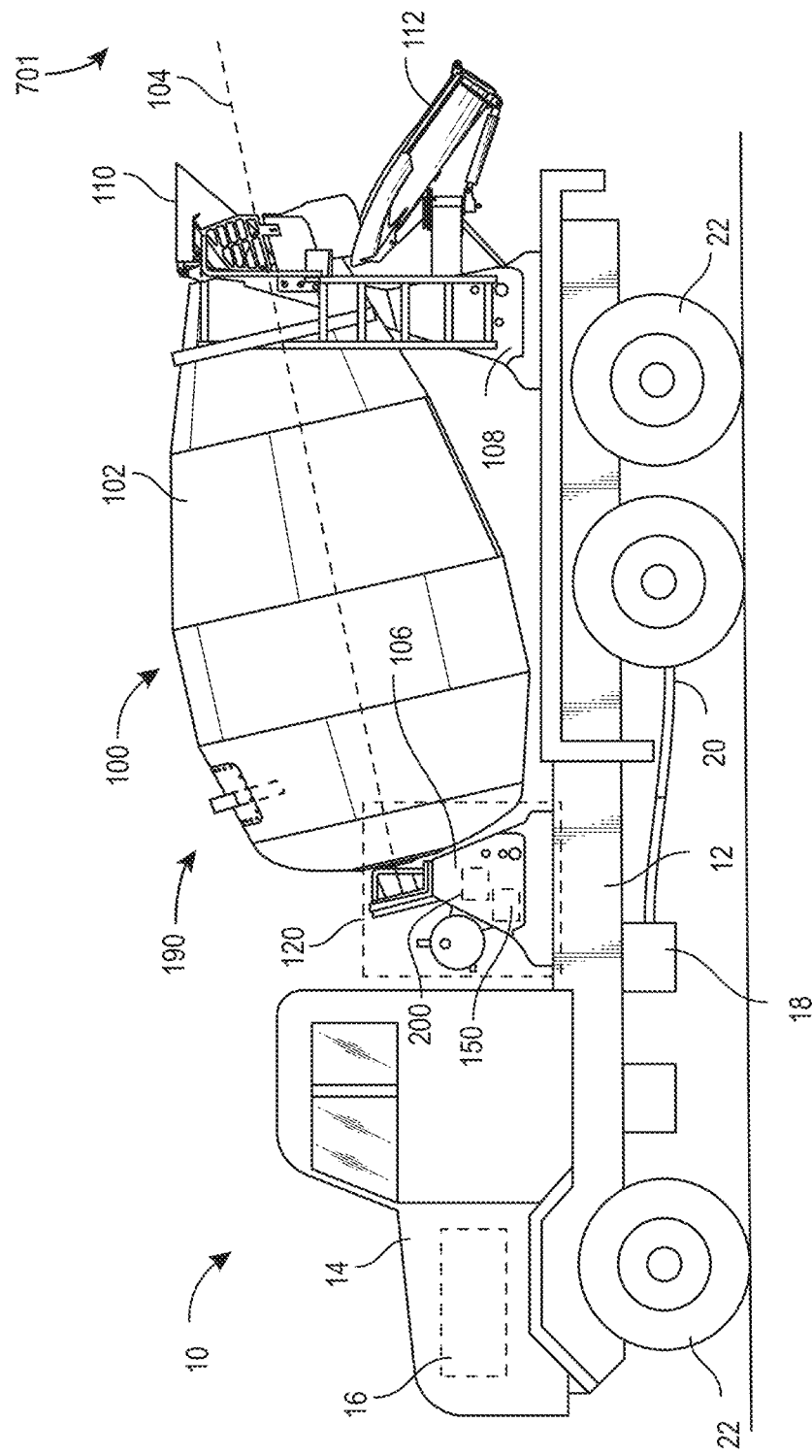
FIG. 6 is a detailed side view of the drum assembly of the concrete mixer truck of FIG. 1, shown to include a sensor assembly, according to an exemplary embodiment.

As shown in FIG. 6, concrete mixer truck 10 includes a concrete sensor assembly (e.g., a mixer sensor, an accelerometer, etc.), shown as sensor assembly 190, according to an exemplary embodiment. Sensor assembly 190 is coupled (e.g., removably, fixedly, attached, etc.) to mixer drum 102 and is configured to measure accelerations. Sensor assembly 190 is communicably connected to sensor controller 200 (e.g., wiredly, wirelessly) and is configured to provide sensor controller 200 with the measured accelerations for analyzing. Sensor controller 200 is configured to analyze measured acceleration signals from sensor assembly 190 to determine any of a type of material present in mixed drum 102, an amount of material present in mixer drum 102, an angle of mixer drum 102, etc., described in greater detail throughout the present disclosure. In some embodiments, sensor controller 200 is communicably connected with drum control system 150. Sensor controller 200 may provide drum control system 150 with any of the determined information for use in controlling mixer drum 102. In some embodiments, sensor controller 200 is positioned on front pedestal 106. In some embodiments, sensor controller 200 is positioned in cab 14. In some embodiments, sensor controller 200 is removably wiredly connected to acceleration sensors of sensor assembly 190. Sensor controller 200 may be communicably connected to a user interface (e.g., a display device, a user input device, etc.) to display any of the determined information to a user (e.g., a vehicle operator), and/or to receive control inputs from the user.

Figure 7:
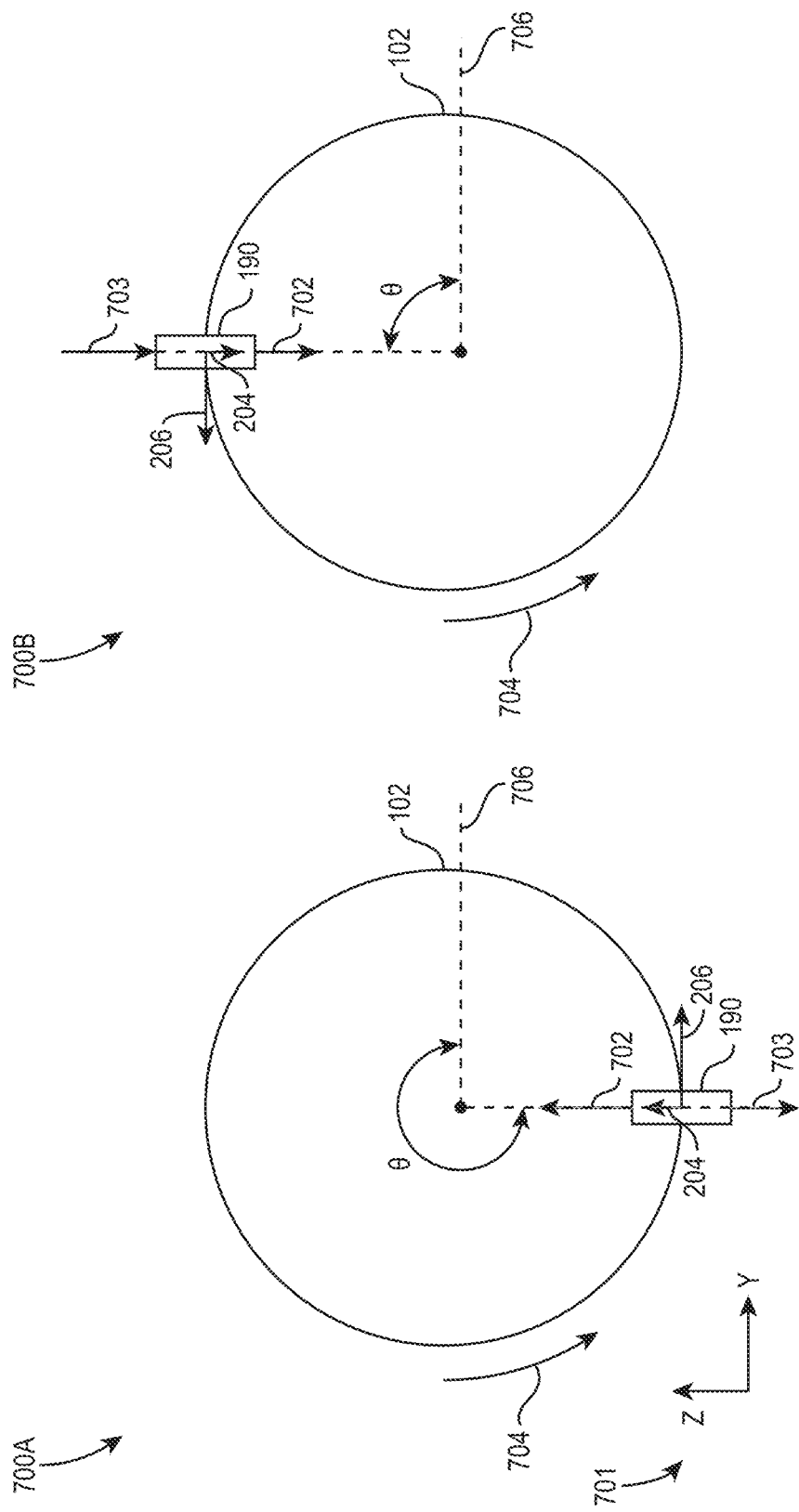
FIG. 7A is a diagram of a cross-sectional view of the drum assembly of the concrete mixer truck of FIG. 1, and the measured accelerations of the sensor assembly of FIG. 6, according to an exemplary embodiment.
FIG. 7B is a diagram of a cross-sectional view of the drum assembly of the concrete mixer truck of FIG. 1, and the measured accelerations of the sensor assembly of FIG. 6, according to an exemplary embodiment.

As shown in FIGS. 6-7B, sensor assembly 190 is configured to measure various accelerations that occur as mixer drum 102 rotates. These accelerations may occur due to deflection of sensor assembly 190, movement of material present in mixer drum 102, inertial forces as mixer drum rotates or accelerates, gravitational acceleration, etc. FIGS. 7A and 7B show sensor assembly 190 measuring gravitational acceleration 703 (g) and centripetal acceleration 702 ($a_c$) as mixer drum 102 rotates in direction 704 or a direction opposite direction 704. When mixer drum 102 is in a position as shown in FIG. 7A, sensor assembly 190 is at a bottom position. When sensory assembly 190 is at the bottom position, gravitational acceleration 703 and centripetal acceleration 702 are in opposite directions along Z-axis of global coordinate system 701. Global coordinate system 701 includes an X-axis, a Z-axis which extends vertically, and a Y-axis. At the bottom position as shown in FIG. 7A, centripetal acceleration 702 along Z axis is in an opposite direction of gravitational acceleration 703. In this way, at the bottom position a minimum acceleration in radial direction 204 is measured, defined as $a_{r,min}$, where $a_{r,min}$ is an acceleration measured by an accelerometer (i.e., a total of gravitational acceleration 703 and centripetal acceleration 702). Likewise, when mixer drum 102 is in the position shown in FIG. 7B, sensor assembly 190 is at a top position. At the top position, gravitational acceleration 703 and centripetal acceleration 702 are in a same direction along radial direction 204. Therefore, a maximum acceleration in the radial occurs when sensor assembly 190 is in the top position, defined as $a_{r,max}$, where $a_{r,max}$ is an acceleration measured by an accelerometer (i.e., a total of gravitational acceleration 703 and centripetal acceleration 702). The minimum and maximum measured accelerations as measured by sensor assembly 190 can be used to determine a position of mixer drum 102.

Advantageously, sensor assembly 190 facilitates determining a position of mixer drum 102, determining an angular speed of mixer drum 102, and counting a number of revolutions of mixer drum 102 over a time period. The methods and techniques used to determine each of these based on acceleration measured by sensor assembly 190 is described in greater detail below.

Figure 8:
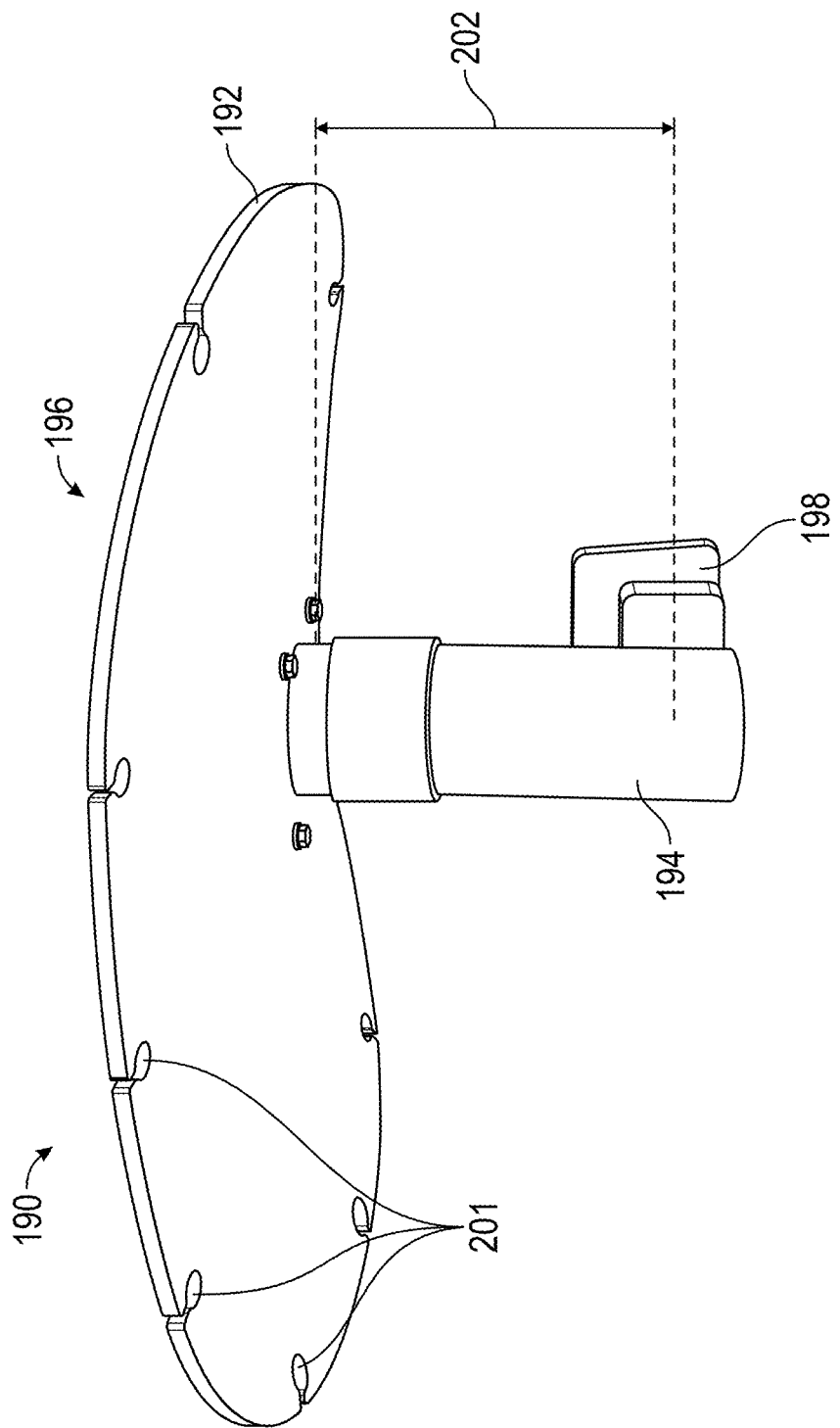
FIG. 8 is a side view of the sensor assembly of FIG. 6, according to an exemplary embodiment.
Figure 9:
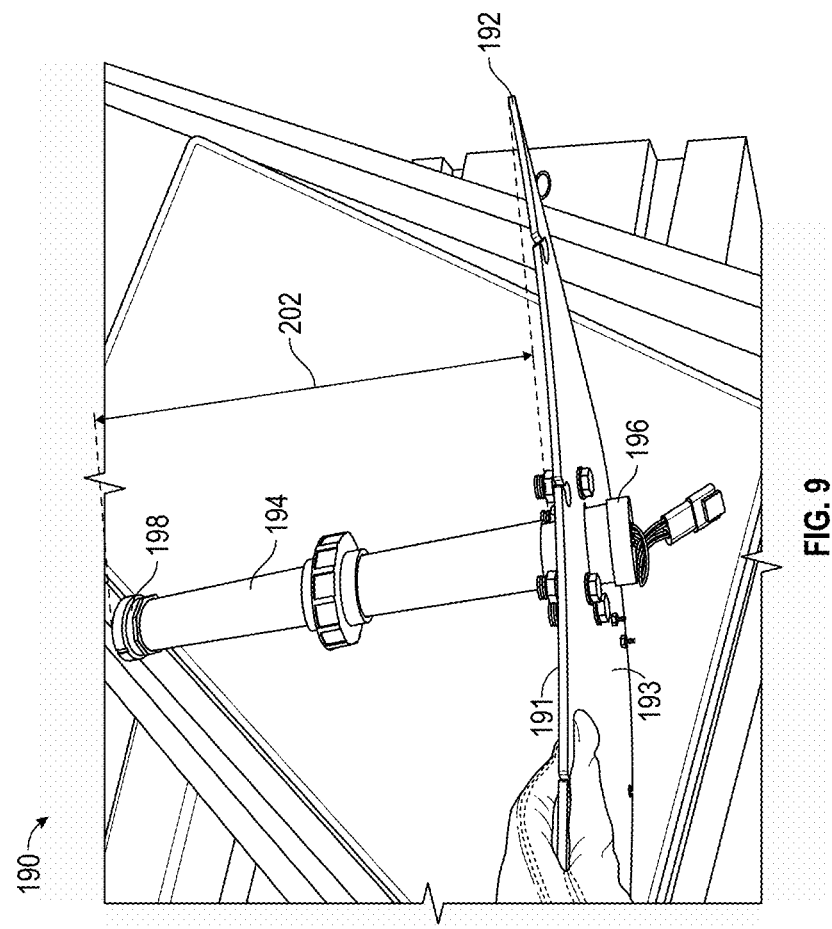
FIG. 9 is a perspective view of the sensor assembly of FIG. 6, according to an exemplary embodiment.
Figure 18:
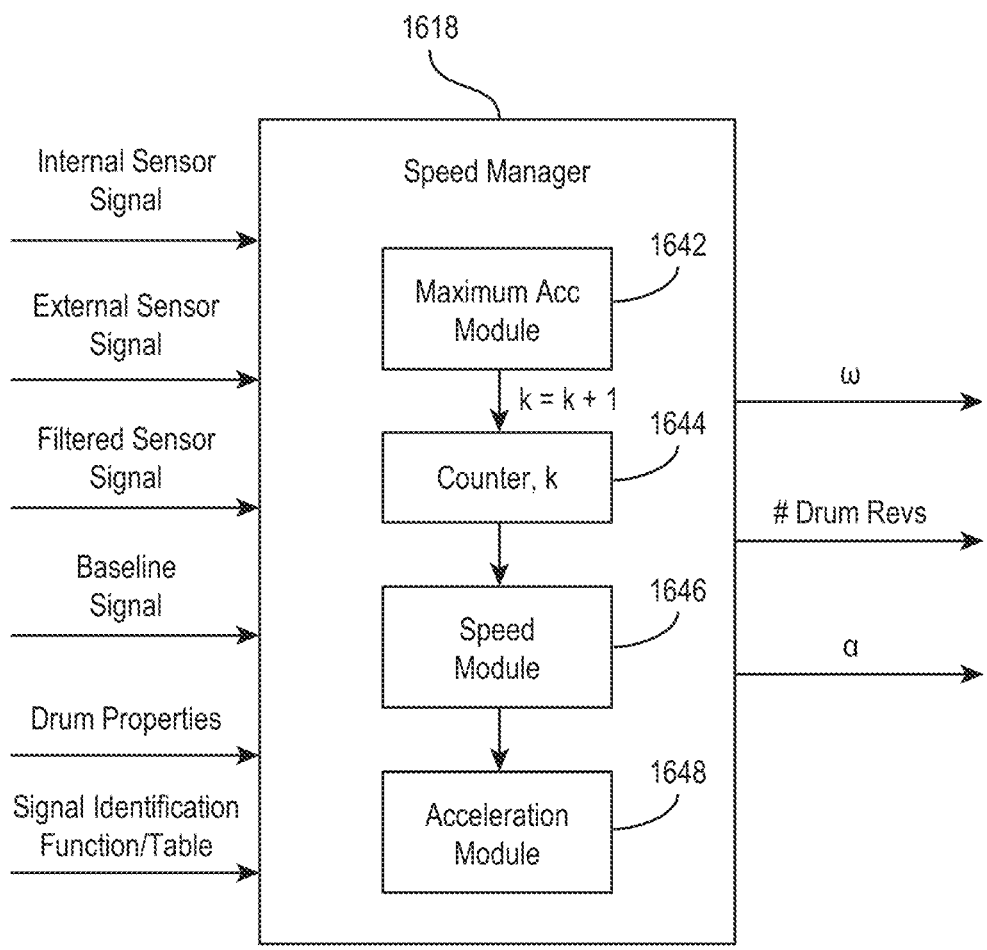
FIG. 18 is a block diagram of the speed manager of the sensor controller of FIG. 10, according to an exemplary embodiment.

As shown in FIGS. 8-9 and 18, sensor assembly 190 includes a hatch portion 192 (e.g., a planar portion, a plate, an elongated portion, an elongated member, etc.) and a protrusion 194 (e.g., a tubular member, an elongated member, a pipe, a beam, a bar, etc.), according to an exemplary embodiment. In some embodiments, protrusion 194 and hatch portion 192 are fixedly coupled (e.g., welded, fastened, riveted, integrally formed, etc.). In some embodiments, protrusion 194 and hatch portion 192 are integrally formed. Protrusion 194 is generally cylindrical. Protrusion 194 extends a distance from hatch portion 192 within mixer drum 102. In some embodiments, protrusion 194 extends a length. In some embodiments, protrusion 194 extends from an interior surface 191 of hatch portion 192. In some embodiments, protrusion 194 extends radially inwards towards axis 104. Hatch portion 192 is configured to couple (e.g., removably via fastener interfaces 201, fixedly, etc.) to mixer drum 102. In some embodiments, protrusion 194 and hatch portion 192 are removably coupled such that protrusion 194 can be removed from hatch portion 192 and mixer drum 102 without requiring removal of hatch portion 192. The removable configuration of protrusion 194 relative to hatch portion 192 and/or the removable configuration of sensor assembly 190 relative to mixer drum 102 facilitates easy access and removal of sensor assembly 190 and/or protrusion 194 for cleaning, replacement, maintenance, etc.

Hatch portion 192 is shown to include an acceleration sensing device (e.g., an accelerometer, a gyroscope, etc.), shown as first acceleration sensor 196. First acceleration sensor 196 may be disposed outside of (e.g., externally) mixer drum 102. In some embodiments, first acceleration sensor 196 is coupled (e.g., removably) to an exterior surface 193 of hatch portion 192. In some embodiments, first acceleration sensor 196 is positioned within protrusion 194. In some embodiments, first acceleration sensor 196 is positioned within an inner volume of protrusion 194 (e.g., if protrusion 194 is at least partially hollow or includes internal spaces, volumes, voids, etc.) and is offset a distance (e.g., 1 inch along a central axis of protrusion 194) from second acceleration sensor 198. In some embodiments, first acceleration sensor 196 is positioned within a housing coupled to protrusion 194 and offset a distance from second acceleration sensor 198. In some embodiments, first acceleration sensor 196 is positioned within an enclosure mounted to an interior surface of mixer drum 102. In some embodiments, first acceleration sensor 196 is configured to measured baseline acceleration signals (e.g., baseline acceleration signals of a firm object such as mixer drum 102). Protrusion 194 includes an acceleration sensing device (e.g., an accelerometer, a gyroscope, etc.) coupled to protrusion 194, shown as second acceleration sensor 198. Second acceleration sensor 198 is disposed a distance 202 from hatch portion 192. Second acceleration sensor 198 may be configured to measure various accelerations inside of mixer drum 102. In some embodiments, second acceleration sensor 198 is configured to measure disturbed acceleration signals due to a presence of material/mixture within mixer drum 102. Likewise, first acceleration sensor 196 may be configured to measure various accelerations outside of mixer drum 102. In some embodiments, first acceleration sensor 196 is configured to measure/produce undisturbed acceleration signals. In some embodiments, first acceleration sensor 196 is positioned according to any of the embodiments described hereinabove and is configured to measure/produce undisturbed acceleration signals. In an exemplary embodiment, first acceleration sensor 196 and second acceleration sensor 198 are both three-axis accelerometers, configured to measure acceleration in three directions (e.g., radial direction 204, tangential direction 206, and a lateral direction). In an exemplary embodiment, both first acceleration sensor 196 and second acceleration sensor 198 are inertial measurement units. First acceleration sensor 196 and second acceleration sensor 198 may be MPU-9250 devices. In some embodiments, second acceleration sensor 198 is covered with a urethane material. Advantageously, this prevents mixture/material (e.g., concrete) present in mixer drum 102 from accumulating/building up on second acceleration sensor 198. In some embodiments, protrusion 194 and second acceleration sensor 198 are coated with a urethane cover.

Hatch portion 192 may be manufactured from steel, aluminum, or any other material which provides sufficient structural strength. Protrusion 194 may also be manufactured from steel, aluminum, or any other material which provides sufficient structural strength. In some embodiments, the material which protrusion 194 is manufactured from, as well as the geometry (e.g., overall length, diameter, shape, etc.) affect accelerations measured by second acceleration sensor 198. For example, if protrusion 194 is manufactured from a rigid material (e.g., steel, brass, iron, etc.), first acceleration sensor 196 may have increased or decreased sensitivity to accelerations. In some embodiments, hatch portion 192 includes one or more seals disposed along a perimeter of an interior surface of hatch portion 192, configured to sealingly interface with mixer drum 102 to prevent material leakage out of mixer drum 102.

In other embodiments (e.g., as shown in FIG. 9), protrusion 194 is manufactured from a flexible material, such as PVC. Additionally, diameter 208 may be inversely proportional to the sensitivity of second acceleration sensor 198. Likewise, an overall length of protrusion 194 may also be inversely proportional to the sensitivity of second acceleration sensor 198. In this way, the material, overall length, diameter, and other geometry of protrusion 194 may be configured to facilitate sufficient acceleration sensitivity yet also facilitate sufficient structural strength for protrusion 194.

Figure 20:
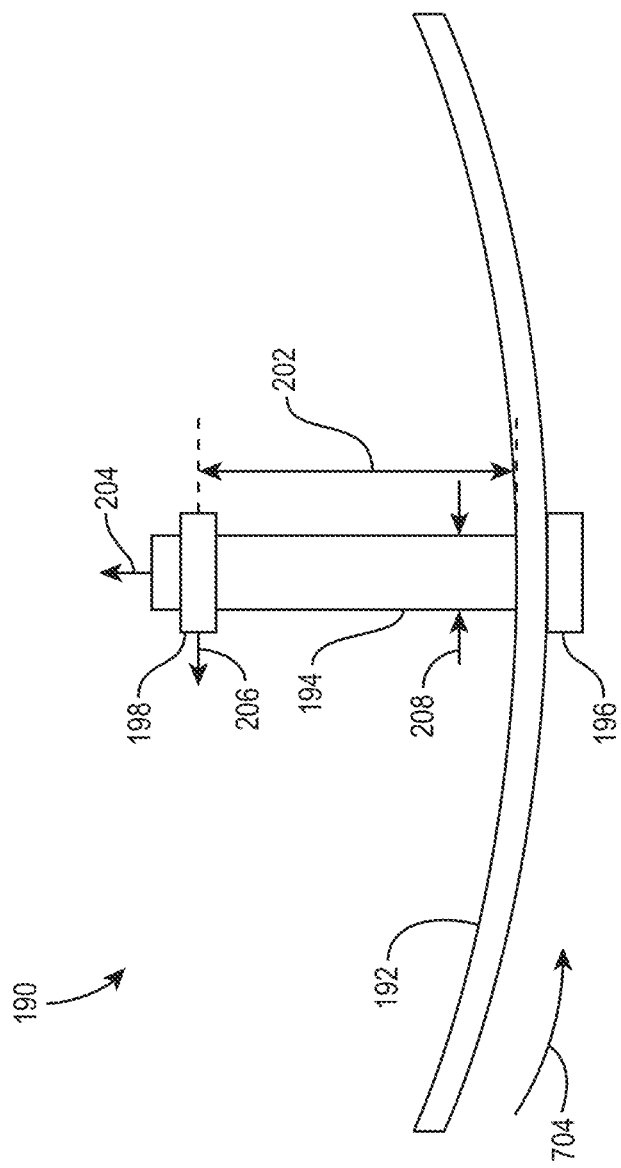
FIG. 20 is a side view of the sensor assembly of FIG. 6, according to an exemplary embodiment.

As shown in FIG. 20, as mixer drum 102 rotates in direction 704 (or in a direction opposite direction 704), second acceleration sensor 198 is configured to measure radial acceleration in radial direction 204, tangential acceleration in tangential direction 206, and lateral acceleration (not shown) within mixer drum 102. If material (e.g., concrete, a slurry, water, debris, etc.) is contained within mixer drum 102 for mixing purposes, signals produced by second acceleration sensor 198 may be disturbed or include noise due to second acceleration sensor 198 and protrusion 194 passing through the material. However, first acceleration sensor 196 is external to mixer drum 102 and therefore does not output a disturbed/noisy signal as second acceleration sensor 198 does. In this way, the signal produced by first acceleration sensor 196 is a "baseline" or "undisturbed" signal, while the signal produced by second acceleration sensor 198 is a "disturbed" or "excited" or "noisy" signal. The disturbed signal produced by second acceleration sensor 198 may be analyzed and/or compared to the undisturbed signal produced by first acceleration sensor 196 to determine various material properties of material within mixer drum 102 and to detect material presence in mixer drum 102. In some cases, certain material properties correspond to various disturbances of the signal produced by second acceleration sensor 198. In some embodiments, the undisturbed signal is used to filter external accelerations out of the disturbed signal. In some embodiments, an amount of noise present in the disturbed or noisy signal produced by second acceleration sensor 198 is related to one or more material properties of the mixture within mixer drum 102.

Figure 13:
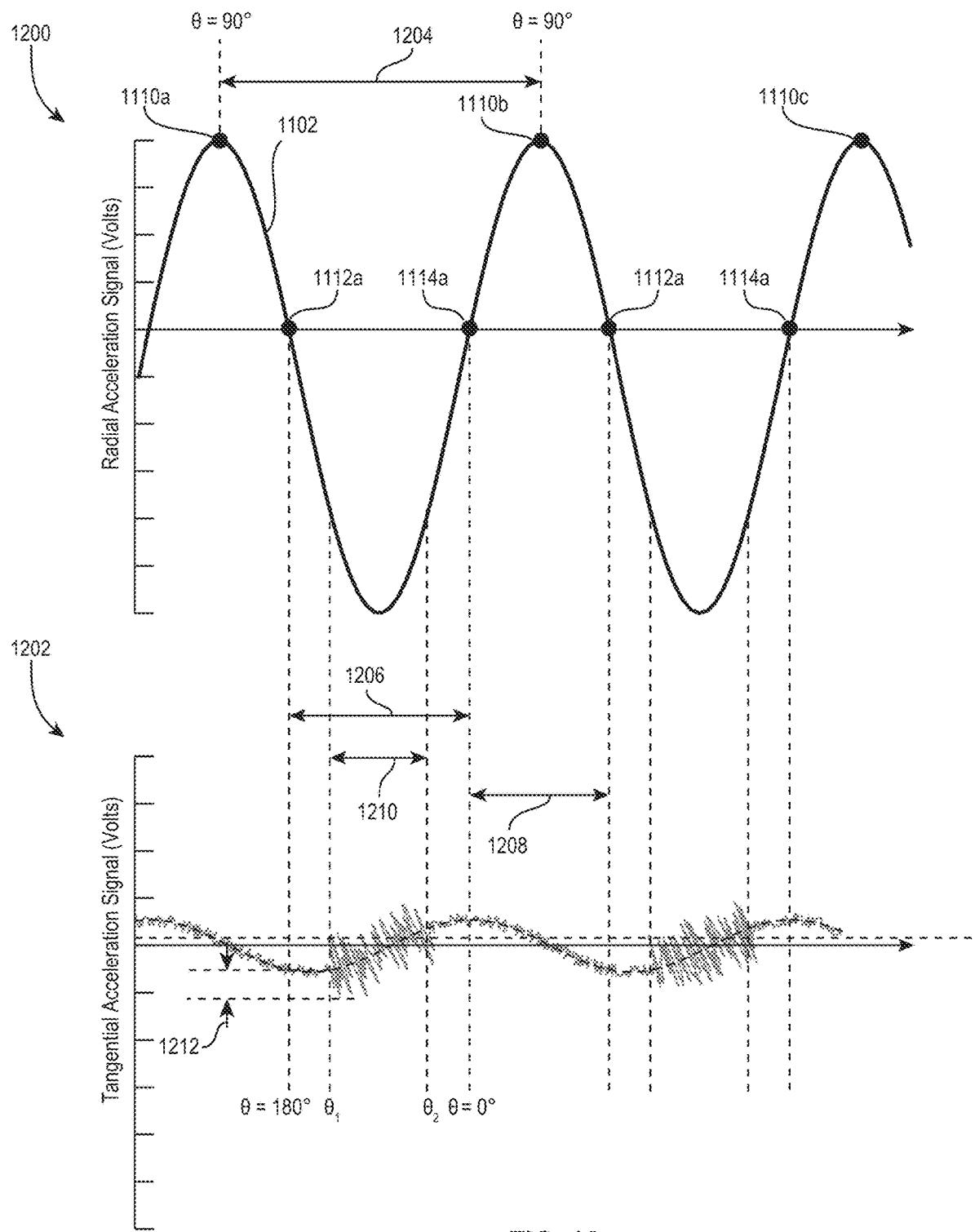
FIG. 13 is a graph of acceleration signals measured by the sensor assembly of FIG. 6, according to an exemplary embodiment.

As shown in FIG. 13, sensor assembly 190 is removably connected to mixer drum 102. Specifically, hatch portion 192 is removably connected with mixer drum 102 via fasteners 210. In some embodiments, sensor controller 200 is coupled to hatch portion 192, as shown in FIG. 13. In some embodiments, a transmission controller is coupled to hatch portion 192, communicably connected to first acceleration sensor 196 and second acceleration sensor 198, and is configured wirelessly communicate (e.g., send information to) sensor controller 200. Mixer drum 102 is shown to include an aperture (e.g., a window, a hole, etc.), shown as aperture 212. Aperture 212 is configured to receive and interface with hatch portion 192. In some embodiments, aperture 212 has a generally same shaped perimeter as hatch portion 192.

Figure 11:
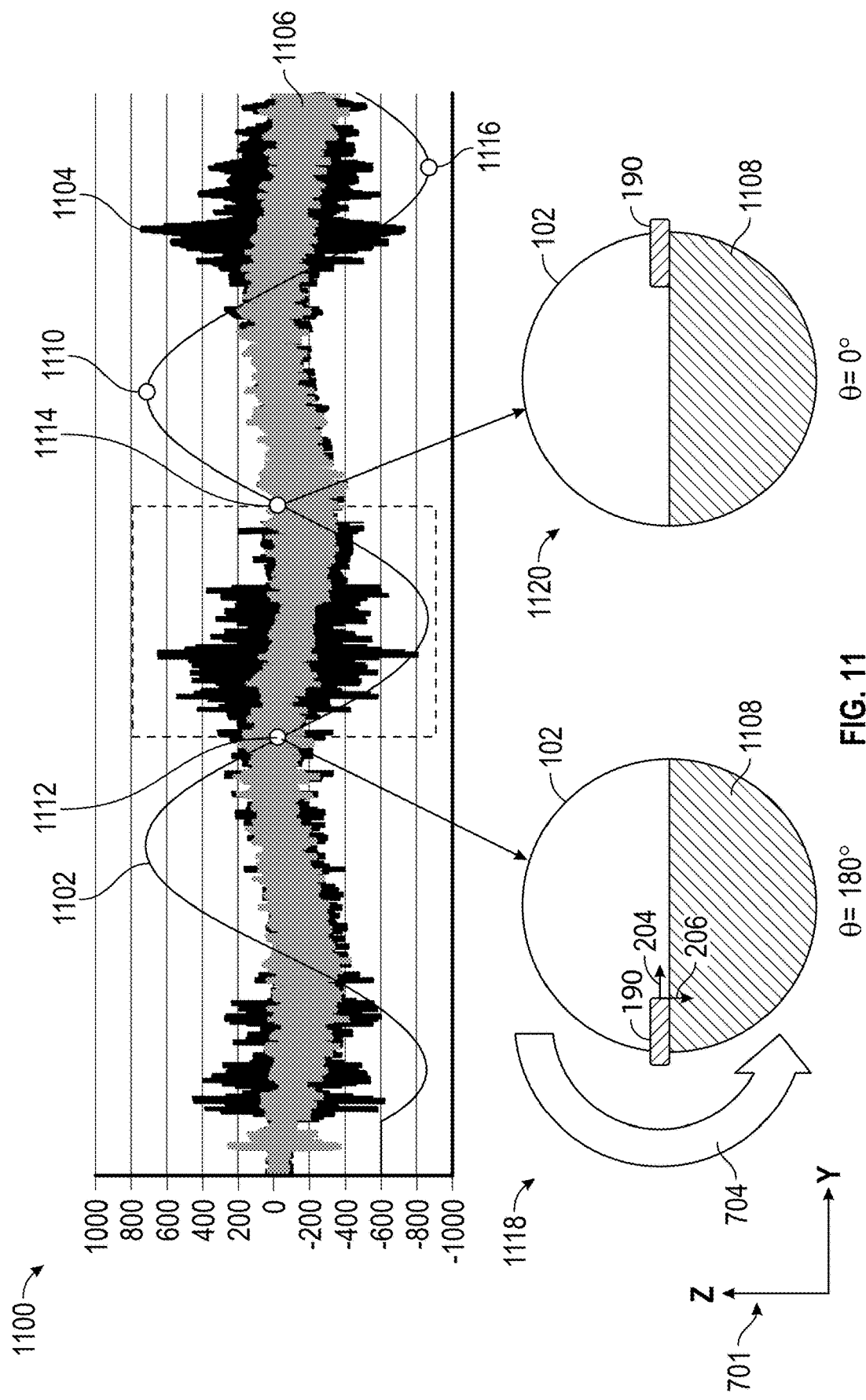
FIG. 11 is a graph of acceleration signals measured by the sensor assembly of FIG. 6, according to an exemplary embodiment.

As shown in FIG. 11, as mixer drum 102 rotates (e.g., in direction 704), the accelerations measured by first acceleration sensor 196 and second acceleration sensor 198 change. Graph 1100 demonstrates the acceleration (Y-axis) with respect to time (X-axis) of mixer drum 102, when mixer drum 102 is rotating at a constant angular speed, ω. Series 1102 of graph 1100 represents acceleration in radial direction 204 measured by either second acceleration sensor 198 with an empty mixer drum 102 or first acceleration sensor 196. Series 1102 is an undisturbed sine wave, illustrating the relationship between time as mixer drum 102 rotates at a constant angular speed, and acceleration in radial direction 204.

As shown in FIG. 11, at point 1112 of series 1102, mixer drum 102 is in the position as represented by diagram 1118. Diagram 1118 shows sensor assembly 190 at a left most position. When sensor assembly 190 is in the left most position, the acceleration measured by sensor assembly 190 in the radial direction is zero, since gravity acts in the negative Z-direction, and series 1102 represents measured acceleration in the radial direction (e.g., radial direction 204). Likewise, at point 1114 of series 1102, sensor assembly 190 is in a right most position (diagram 1120), and the acceleration measured by sensory assembly 190 in the radial direction is zero for the same reasons as why the radial acceleration measured by sensory assembly 190 is zero in the left most direction.

At point 1110 of series 1102, sensor assembly 190 is in the upper most position as shown in FIG. 7B above. At point 1110, the radial acceleration as measured by sensor assembly 190 is maximum, since gravity acts entirely in the radial direction towards a center of mixer drum 102. Therefore, the measured radial acceleration at point 1110 is approximately:

$$a_{r,max} = g$$

where g is acceleration due to gravity (gravitational acceleration 703).

Similarly, at point 1116 of series 1102, sensor assembly 190 is at a bottom most point and both gravitational acceleration 703 and gravity acts in a negative radial direction. This produces a minimum (i.e., a maximum negative) radial acceleration as measured by sensor assembly 190. Consequently, at point 1116 of series 1102, the measured radial acceleration is approximately:

$$a_{r,min} = -g$$

As shown in FIG. 11, mixer drum 102 may contain material (e.g., cement, a slurry, a cement-water mixture, rocks, etc.), shown as mixture 1108, according to an exemplary embodiment. As mixer drum 102 rotates, a portion of sensor assembly (e.g., protrusion 194 and second acceleration sensor 198) passes through mixture 1108. This causes acceleration measured by second acceleration sensor 198 to be noisy (e.g., disturbed). The measured acceleration may be particularly noisy for acceleration measured in tangential direction 206. When sensor assembly 190 travels through mixture 1108, an amount of noise is increased. However, when sensor assembly 190 travels through open areas of mixer drum 102, the amount of noise is decreased. The amount of noise can be used to determine a type of mixture 1108, a consistency of mixture 1108, a volume, mass, weight, etc., of mixture 1108. The methods and techniques used to determine any of these is described in greater detail below.

Series 1104 of graph 1100 illustrates a mixture 1108 having some amount of water, according to an exemplary embodiment. Series 1106 of graph 1100 illustrates a mixture 1108 without water. Both series 1104 and series 1106 illustrate tangential acceleration measured by sensor assembly 190. In particular, series 1104 and series 1106 illustrate tangential acceleration as measured by second acceleration sensor 198. Both series 1104 and series 1106 show a noisy signal. It can be seen that series 1104 which represents a mixture having some amount of water is noisier than series 1106 which represents a mixture having no water. The amount of noise may be used to determine a type of mixture 1108, according to some embodiments. In some cases, the amount of noise associated with the tangential acceleration as measured by second acceleration sensor 198 is used to determine any properties of mixture 1108 such as a of a slump of mixture 1108, a consistency of mixture 1108, or homogeneity of mixture 1108.

Figure 12:
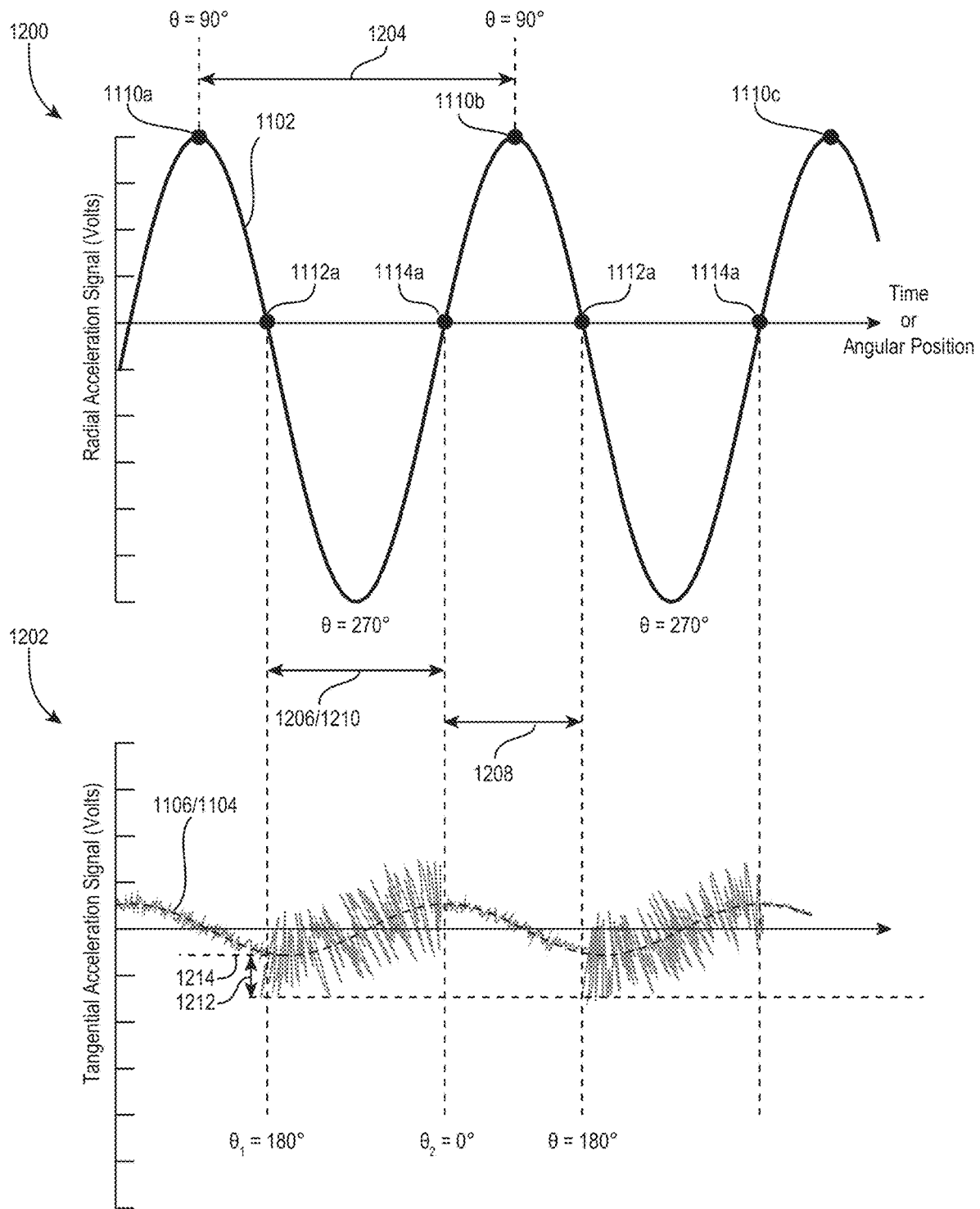
FIG. 12 is a graph of acceleration signals measured by the sensor assembly of FIG. 6, according to an exemplary embodiment.

As shown in FIG. 12, graph 1200 illustrates series 1102, and graph 1202 illustrates either series 1106 or series 1104, according to an exemplary embodiment. Series 1102 is shown having a sinusoidal shape. Series 1102 illustrates radial acceleration (e.g., radial acceleration as measured by first acceleration sensor 196, Y-axis) with respect to time or angular position. Graph 1200 and graph 1202 include a first portion defined from θ=180° to θ=0° and a second portion 1208 defined from θ=0° to θ=180°. First portion 1206 represents when sensor assembly 190 is between the positions shown in diagram 1118 and diagram 1120 while travelling in direction 704, and second portion 1208 represents when sensor assembly 190 is between the positions shown in diagram 1120 and diagram 1118 while travelling in direction 704.

In some embodiments, tangential acceleration as measured by second acceleration sensor 198 as a voltage signal. For example, series 1106/1104 may have units of voltage which correspond to acceleration. A signal to noise ratio 1212 of series 1106/1104 or a maximum perturbation can be measured as shown. In some embodiments, signal to noise radio 1212 is calculated using the following equation:

$$SNR_{dB} = 20 \cdot \log_{10} \frac{V_{signal,RMS}}{V_{noise,RMS}}$$

where $SNR_{dB}$ is the signal to noise ratio in decibels, $V_{signal,RMS}$ is a root mean square voltage of an undisturbed signal (e.g., a value or an average of values of a voltage associated with second portion 1208, represented by value 1214), and $V_{noise,RMS}$ is a root mean square voltage value (e.g., a voltage value corresponding to a noisy tangential acceleration) of series 1106/1104. When sensor assembly 190 passes through mixture 1108, an amount of noise associated with the voltage signal corresponding to tangential acceleration increases, as shown by the noisy signal (series 1106/1104) in first portion 1206. In this way, regions with a low signal to noise ratio identify that mixture is present, and regions with a high signal to noise ratio (e.g., second portion 1208) identify that mixture is not present in that part of mixer drum 102. In other embodiments, regions with a high signal to noise ratio identify that mixture is present, and regions with a low signal to noise ratio identify that mixture is not present in that part of mixer drum 102. In this way, the signal to noise ratio can be used to determine the presence of material in mixer drum 102 (e.g., by identifying areas with high signal to noise ratio or areas with low signal to noise ratio).

Using the measured accelerations, an initial angle and a final angle associated with regions of mixer drum 102 which contain mixture 1108 can be determined. In the example shown in FIG. 12, it can be seen that first portion 1206 has a high amount of noise (e.g., a low signal to noise ratio), while second portion 1208 has a low or negligible amount of noise (e.g., a high signal to noise ratio). Since first portion 1206 is defined from θ=180° to θ=0°, it can be determined that mixture/material is present from θ=180° to θ=0° of mixer drum 102 (e.g., mixer drum 102 is half full).

In some cases, an initial angle, $θ_1$ is recorded if an amount of noise (e.g., a signal to noise ratio) of the signal associated with the tangential acceleration as measured by second acceleration sensor 198 (e.g., series 1106/1104) exceeds a predetermined threshold amount. The initial angle may be recorded if the following condition for the tangential acceleration signal is met:

If: $SNR_{current} > SNR_{threshold}$ Then: $θ_{current} = θ_1$

In some cases, mixer drum 102 continues to rotate until the amount of noise (e.g., the signal to noise ratio) of the signal associated with the tangential acceleration as measured by second acceleration sensor 198 falls below the predetermined threshold amount. For example, as mixer drum 102 continues to rotate through the region containing mixture/material, a final angle, $θ_2$ is recorded if the following condition for the tangential acceleration signal is met:

If: $SNR_{current} < SNR_{threshold}$ Then: $θ_{current} = θ_2$

In this way, an initial angle, $θ_1$, and a final angle, $θ_2$, between which mixture/material is present can be determined.

Various properties (e.g., circumference, radius, diameter, total volume, etc.) of mixer drum 102 as well as the initial angle and the final angle can be used to approximate a volume of mixture/material present in mixer drum 102. In some embodiments, the volume of material/mixture present in mixer drum 102 can be approximated using a function shown as:

$$V_{mixture} = f_{volume}(θ_1, θ_2, r_{drum}, V_{drum})$$

where $V_{mixture}$ is a volume of mixture present in mixer drum 102, $r_{drum}$ is a radius of mixer drum 102, and $V_{drum}$ is a volume of mixer drum 102. In some embodiments, function $f_{volume}$ is determined using empirical data. In some embodiments, function $f_{volume}$ is determined based on geometric relationships of mixer drum 102.

The magnitude of noise present in tangential voltage signal is proportional to a slump of the mixture present in mixer drum 102, according to an exemplary embodiment. In this way, a slump of the mixture present in mixer drum 102 can be correlated to the magnitude of noise (e.g., the magnitude of a signal to noise ratio). In some embodiments, the relationship between the magnitude of the noise and the slump is defined according to a linear equation, shown as:

$$\frac{1}{S} = m \cdot M_{noise} + b$$

where S is a slump of the mixture (e.g., psi, inches, etc.), m is a slope constant determined empirically, $M_{noise}$ is a magnitude of noise (e.g., a signal to noise ratio) of a noisy acceleration signal (e.g., tangential acceleration signal as measured by second acceleration sensor 198) relative to an undisturbed/clean acceleration signal (e.g., a tangential acceleration signal as measured by first acceleration sensor 196), and b is an intercept constant determined empirically. The empirical constants may be determined through testing to determine the linear relationship between slump of the mixture and the magnitude of the signal noise.

Put more generally, the slump of the mixture may be determined based on magnitude of noise of an acceleration signal, shown as:

$$S = f_{slump}(M_{noise})$$

where $f_{slump}$ is an empirical relationship determined through testing. In some embodiments, $f_{slump}$ is a linear relationship, as shown above. In some embodiments, $f_{slump}$ is a non-linear relationship (e.g., exponential, polynomial, logarithmic, etc.).

It should be noted that the radial acceleration signal (represented by series 1102) and the tangential acceleration signal (represented by series 1106/1104) are phase-shifted 90 degrees relative to each other. This is due to the fact that radial direction 204 and tangential direction 206 are normal to each other. Due to this, the maximum acceleration (due to gravity) for the tangential acceleration occurs at points 1112 and 1114 which correspond to the orientations of mixing drum 102 as shown in diagram 1118 and diagram 1120. When mixing drum 102 is in the orientation as shown in diagram 1118, gravity acts in tangential direction 206, and when mixing drum 102 is in the orientation as shown in diagram 1120, gravity acts in a direction opposite tangential direction 206. Therefore, in these orientations, tangential acceleration has maximum and minimum values respectively as shown in graph 1202.

As shown in FIG. 13, $\theta_1$ and $\theta_2$ are not necessarily 180 and 0 degrees, respectively, due to the amount of mixture present in mixer drum 102, according to an exemplary embodiment. For example, as shown in FIG. 13, $\theta_1$ is a value other than 180 degrees, and $\theta_2$ is a value other than 0 degrees. Both $\theta_1$ and $\theta_2$ may be determined similarly as described in greater detail above with reference to FIG. 12. However, in the example shown in FIG. 13, $\theta_1$ is a value less than 180 degrees, and $\theta_2$ is a value greater than 0 degrees. This indicates that less mixture is present in mixer drum 102, since mixture portion 1210 as shown in FIG. 13 is less than mixture portion 1210 as shown in FIG. 12, due to the fact that $\theta_1$ and $\theta_2$ define a smaller range of angles over which a significant amount of noise is present. This indicates that sensor assembly 190 is not in contact with the mixture for a longer time than as shown in FIG. 12, which indicates that less mixture is present in mixer drum 102.

Referring again to FIG. 12, the measured radial (or tangential) acceleration as shown in graph 1200 can be used to determine an amount of revolutions of mixer drum 102 over a time period, according to an exemplary embodiment. For example, a period 1204 is defined between point 1110a and point 1110b. In some embodiments, a number of times point 1110 is reached (e.g., a number of periods 1204) over a time period determines a number of revolutions of mixer drum 102. Both point 1110a and point 1110b indicate an orientation of mixer drum 102 as shown in FIG. 7B, therefore, every time mixer drum 102 reaches the orientation as shown in FIG. 7B (and indicated by points 1110), a revolution has been completed. In some embodiments, a number of times mixer drum 102 reaches the orientation as shown in FIG. 7B are counted (e.g., by counting a number of times point 1110 is reached or by counting a number of peaks of series 1102) over a time period to determine a number of revolutions of mixer drum 102 over the time period. The number of revolutions of mixer drum 102 and the time period can be used to determine an average angular velocity of mixer drum 102 over the time period using the equation:

$$\omega = \frac{\text{\# revolutions}}{\Delta t}$$

where $\Delta t$ is a time duration of the time period, and #revolutions is a number of revolutions of mixer drum 102 over the time period.

Figure 14:
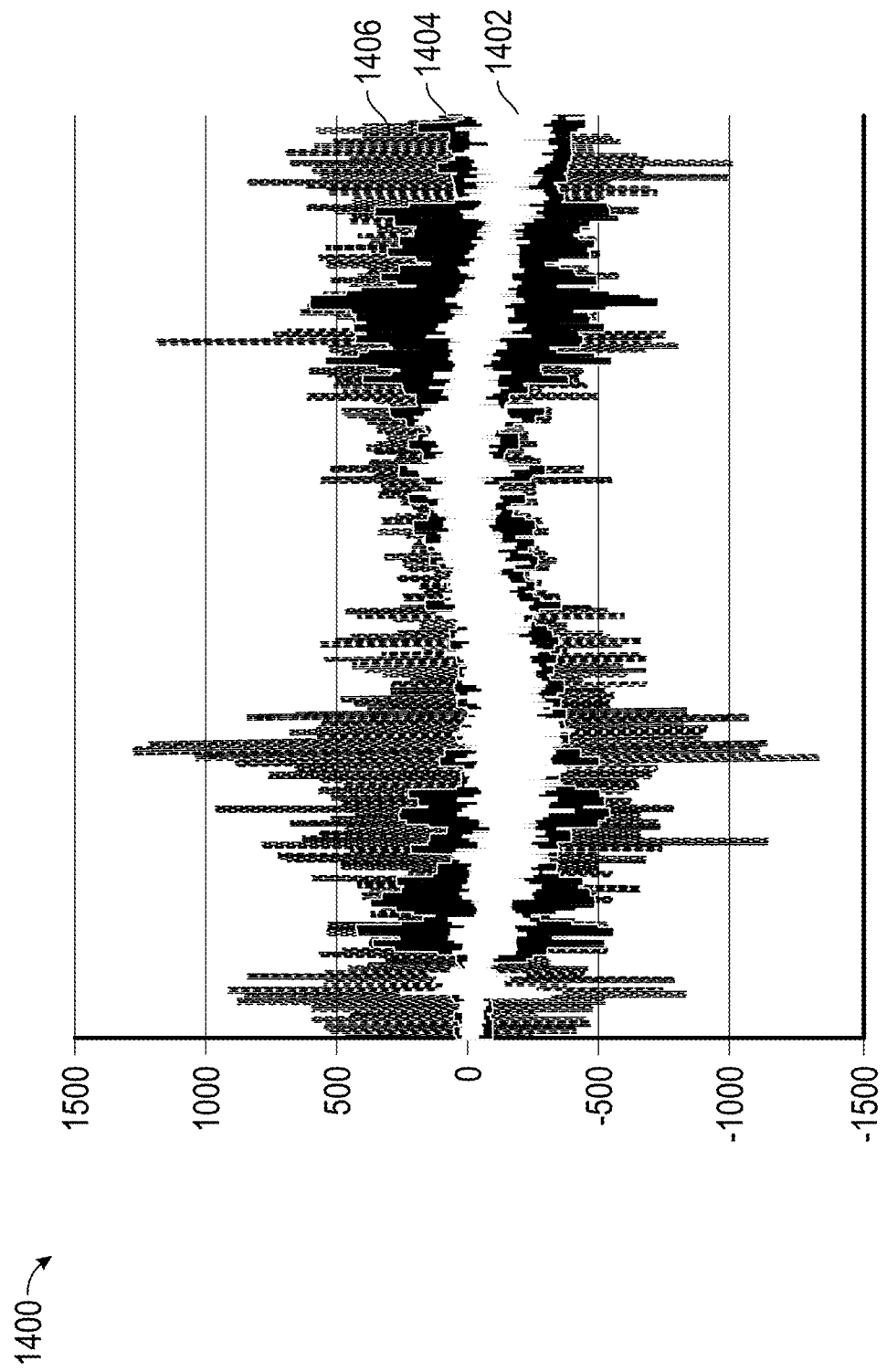
FIG. 14 is a graph of acceleration signals measured by the sensor assembly of FIG. 6, according to an exemplary embodiment.
Figure 15:
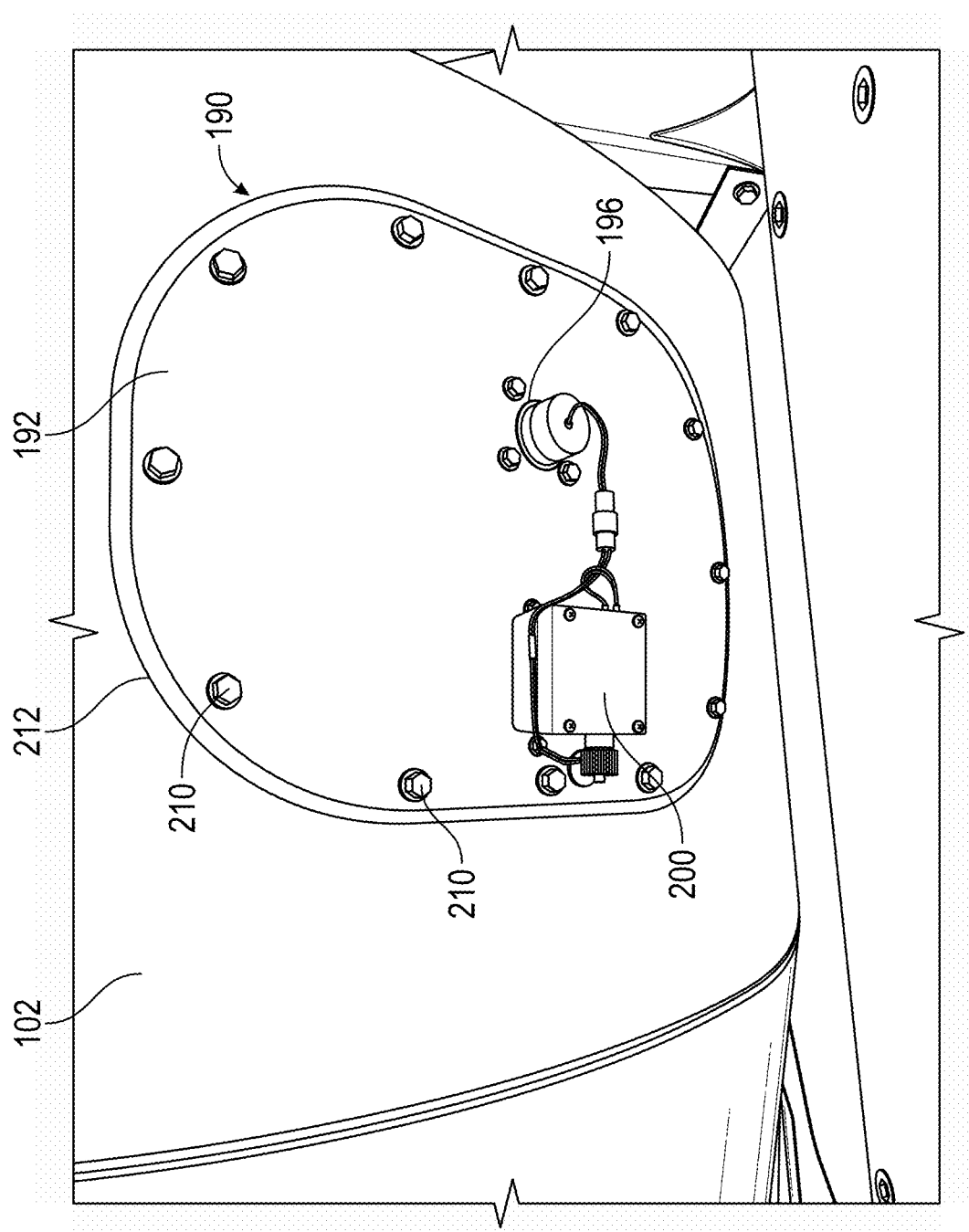
FIG. 15 is a perspective view of the sensor assembly of FIG. 6 installed in the mixer drum of FIG. 6, according to an exemplary embodiment.

Referring now to FIG. 14, graph 1400 shows acceleration data received from second acceleration sensor 198 for various types of materials, according to an exemplary embodiment. Graph 1400 includes series 1402, series 1404, and series 1406. Series 1402 shows an acceleration signal received from sensor assembly 190 associated with an empty mixer drum 102. Series 1404 shows an acceleration signal received from sensor assembly 190 associated with mixer drum 102 containing water. Series 1406 shows an acceleration signal received from sensor assembly 190 associated with mixer drum 102 containing mud. As shown in FIG. 14, when mixer drum 102 contains mud (series 1406), the acceleration signal is noisier as compared to when mixer drum 102 contains water (series 1404). Series 1402 which represents empty mixer drum 102 has a least amount of noise compared to series 1404 and series 1406. In this way, the magnitude of the noise, when/where the noise occurs, the noise characteristics, etc., can be used to accurately identify different material types/properties present in mixer drum 102.

Figure 10:
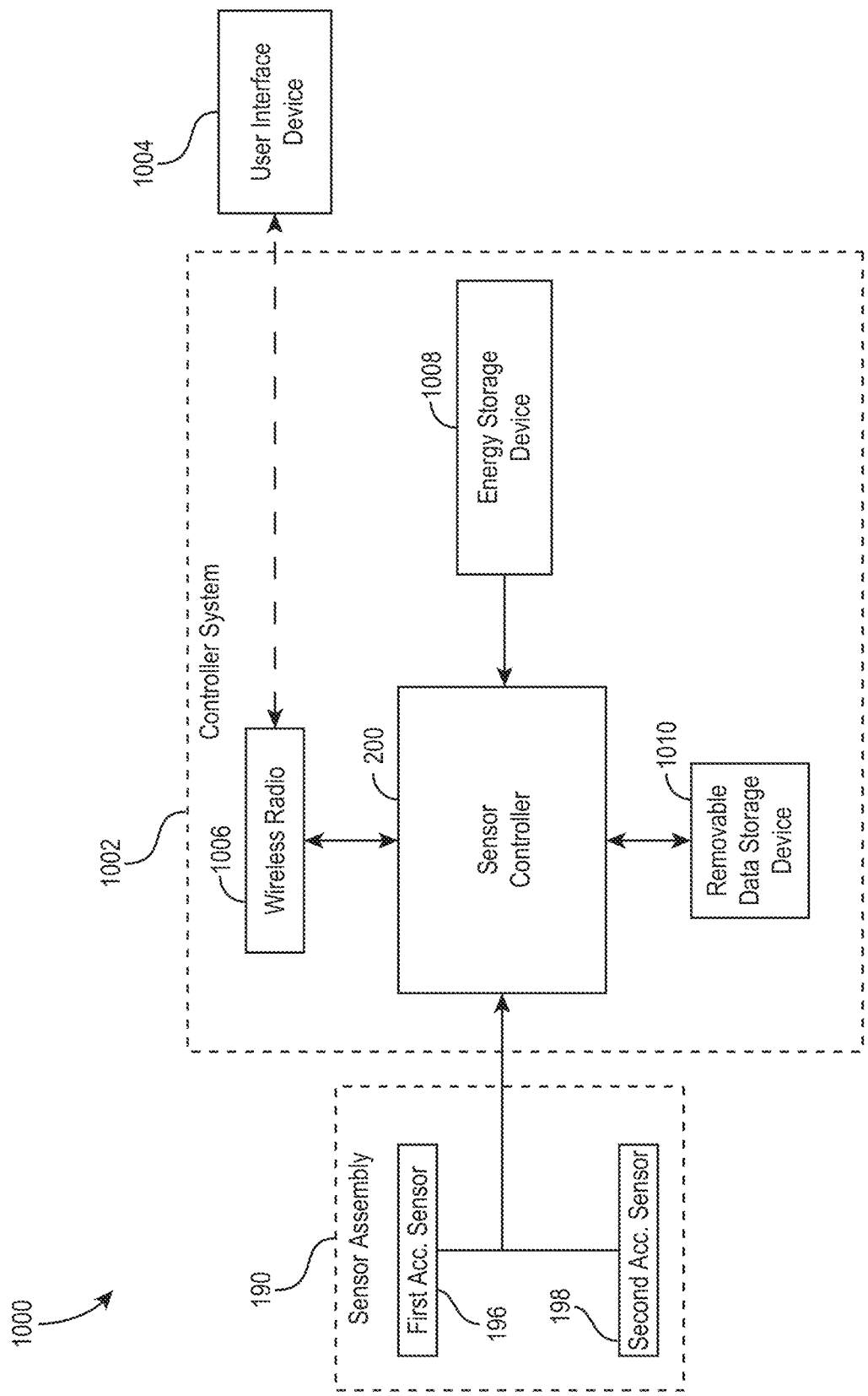
FIG. 10 is a block diagram of a sensor system which includes the sensor assembly of FIG. 6 and a sensor controller, according to an exemplary embodiment.

Referring now to FIG. 10, a system (e.g., an electronic system, a control system, etc.), shown as control system 1000 is used to monitor, analyze, and display acceleration information measured by sensor assembly 190, and more particularly, acceleration information measured by first acceleration sensor 196 and second acceleration sensor 198, according to an exemplary embodiment. System 1000 is shown to include sensor assembly 190 and controller system 1002. Sensor assembly 190 includes first acceleration sensor 196 and second acceleration sensor 198 communicably connected with sensor controller 200. First acceleration sensor 196 and second acceleration sensor 198 may provide sensor controller 200 with an acceleration signal (e.g., any of radial acceleration, tangential acceleration, lateral acceleration). Sensor controller 200 is configured to analyze the acceleration signals using any of the techniques described above, or described in greater detail below with reference to FIGS. 16-19. In some embodiments, sensor controller 200 is an Arduino UNO, or any other processing circuit, microcontroller, microprocessor, etc. In some embodiments, first acceleration sensor 196 and second acceleration sensor 198 are MPU-9250 9-axis accelerometer/gyroscope/compass devices, configured to measure acceleration in any direction, including but not limited to, radial direction 204, tangential direction 206, and a lateral direction normal to both radial direction 204 and tangential direction 206.

Controller system 1002 includes a data storage device, shown as removable data storage device 1010, communicably connected with sensor controller 200, according to an exemplary embodiment. Removable data storage device 1010 is any data storage device configured to store any of time-series data of acceleration as measured by sensor assembly 190 (e.g., by at least one of first acceleration sensor 196 and second acceleration sensor 198), information determined by sensor controller 200, and various functions, relationships, tables, profiles, etc., used by sensor controller 200 to analyze the acceleration information received from sensor assembly 190. In some embodiments, removable data storage device 1010 is a Secure Digital Memory Card. Removable data storage device 1010 may be any of a CD-ROM, a USB flash drive, an external hard drive, etc. In some embodiments, removable data storage device 1010 is a component of sensor controller 200. In some embodiments, removable data storage device 1010 is any other device configured to store information and be communicably connected with sensor controller 200. In some embodiments, removable data storage device 1010 is an SD card and is configured to communicably connect with sensor controller 200 through a serial peripheral interface (SPI).

Controller system 1002 includes an energy provider (e.g., a battery, a power source, an outlet, etc.), shown as energy storage device 1008, according to an exemplary embodiment. Energy storage device 1008 is configured to store energy (e.g., in chemical form, electrical form, etc.), and provide electrical energy to sensor controller 200. In some embodiments, energy storage device 1008 is a battery configured to start engine 16. In some embodiments, energy storage device 1008 is a battery. In some embodiments, energy storage device 1008 is a component of sensor controller 200. In some embodiments, energy storage device 1008 is a rechargeable USB battery pack, and provides sensor controller 200 with power through a USB interface.

Controller system 1002 includes a wireless transceiver (e.g., a Bluetooth radio, a LoRa radio, a ZigBee radio, a WiFi transceiver, etc.), shown as wireless radio 1006, according to an exemplary embodiment. Wireless radio 1006 is communicably connected with a display device (e.g., a screen, a touchscreen, a control interface, a button interface, a display, etc.), shown as user interface device 1004, according to an exemplary embodiment. In some embodiments, wireless radio 1006 is communicably connected with sensor controller 200 and facilitates the transmission of data/information between sensor controller 200 and user interface device 1004. In some embodiments, wireless radio 1006 is configured to transmit information between user interface device 1004 and sensor controller 200 regarding any of acceleration data as measured by sensor assembly 190, data/information (e.g., time-series acceleration data) stored in removable data storage device 1010, and various information determined by sensor controller 200 (e.g., material type present in mixer drum 102, speed of mixer drum 102, position of mixer drum 102, number of revolutions of mixer drum 102, consistency of mixture/material present in mixer drum 102, volume of mixer/material present in mixer drum 102, etc.). In some embodiments, wireless radio 1006 is an external device, removably connected to sensor controller 200 to facilitate communication between sensor controller 200 and user interface device 1004. In some embodiments, wireless radio 1006 is configured to communicate any of the hereinabove information to a remote server. In some embodiments, wireless radio 1006 facilitates communication between sensor controller 200 and the Internet. In some embodiments, wireless radio 1006 is or includes a cellular dongle, configured to communicably connect sensor controller 200 with a cellular tower. In some embodiments, wireless radio 1006 is a component of sensor controller 200. In some embodiments, sensor controller 200 is wiredly connected to user interface device 1004. In some embodiments, wireless radio 1006 is an ESP32 Wi-Fi microcontroller, configured to facilitate wireless communication between sensor controller 200 and user interface device 1004. In some embodiments, wireless radio 1006 is configured to communicably connect with sensor controller 200 via universal asynchronous receiver-transmitter (UART).

User interface device 1004 is configured to display information received from wireless radio 1006, according to an exemplary embodiment. User interface device 1004 may display any of the information received from wireless radio 1006 and/or sensor controller 200 to a user. In some embodiments, user interface device 1004 includes one or more display screens which include a Graphical User Interface (GUI) to provide any of the information received from wireless radio 1006 and/or sensor controller 200 to a user. In some embodiments, user interface device 1004 is a wirelessly communicable device and is configured to wirelessly communicate with wireless radio 1006. In some embodiments, user interface device 1004 is a smart-phone (e.g., an Android smart phone), a tablet (e.g., an Android tablet), etc.

Figure 16:
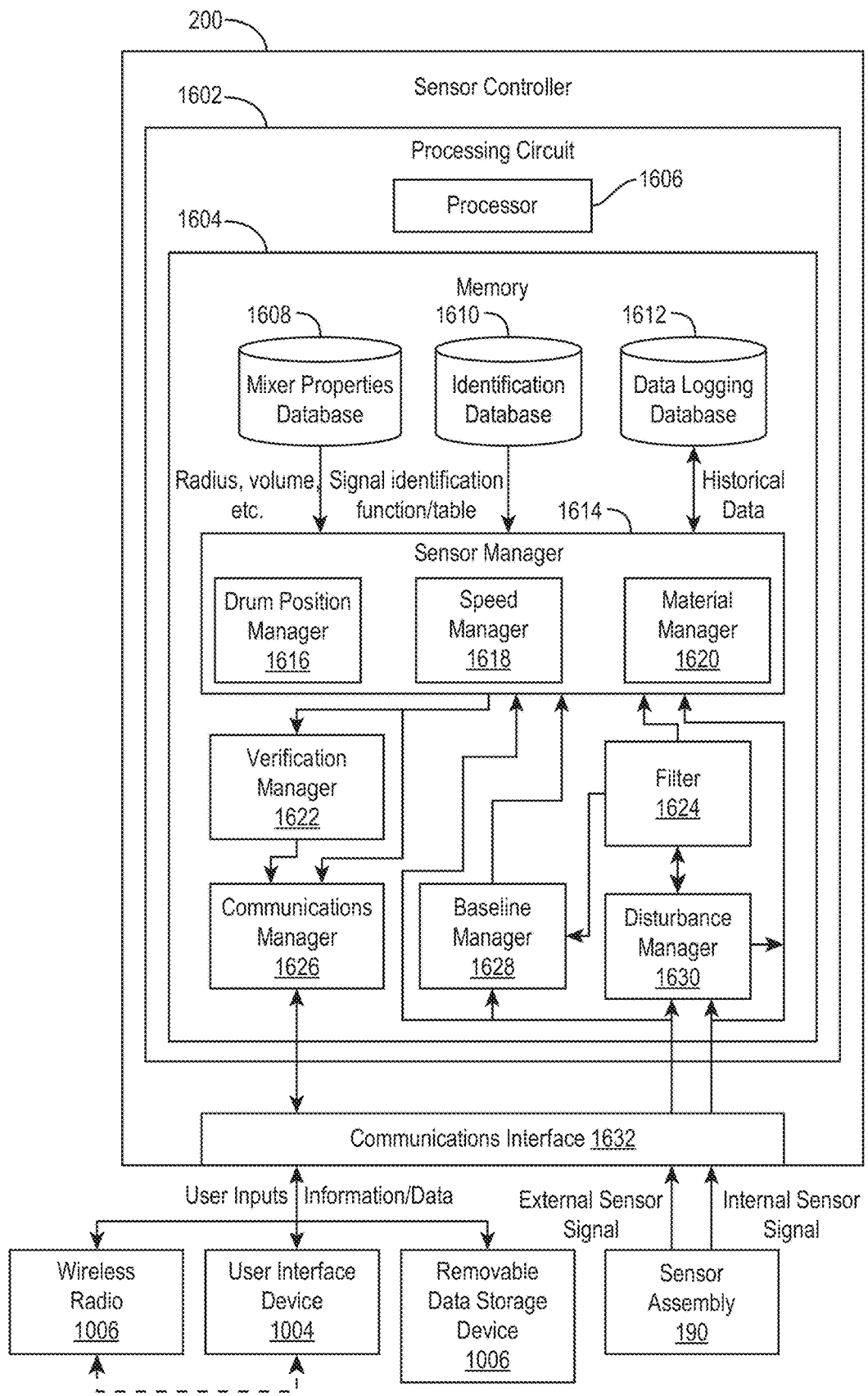
FIG. 16 is a block diagram of the sensor controller of FIG. 10, shown to include a material manager, a speed manager, and a drum speed manager, according to an exemplary embodiment.

Referring now to FIG. 16, sensor controller 200 is shown in greater detail, according to an exemplary embodiment. Sensor controller 200 is shown to include a communications interface 1632 and a processing circuit 1602. Communications interface 1632 may include wired or wireless interfaces (e.g., jacks, antennas, transmitters, receivers, transceivers, wire terminals, etc.) for conducting data communications with various systems, devices, or networks. For example, communications interface 1632 may include an Ethernet card and port for sending and receiving data via an Ethernet-based communications network and/or a Wi-Fi transceiver for communicating via a wireless communications network. Communications interface 1632 may be configured to communicate via local area networks or wide area networks (e.g., the Internet, a building WAN, etc.) and may use a variety of communications protocols (e.g., BACnet, IP, LON, etc.). In some embodiments, any of the components and functionality of sensor controller 200 are implemented at a remote device (e.g., a remote server). In some embodiments, sensor controller 200 includes a wireless radio (e.g., a transmitter, a transceiver, a cellular dongle, a wirelessly communicable device, etc.), configured to wirelessly communicate with a remote device (e.g., a remote server). In some embodiments, sensor controller 200 transmits any information received through communications interface 1632 to the remote device. In some embodiments, the remote device is configured to perform any of the functionality and techniques of sensor controller 200 (e.g., determine material properties such as homogeneity, slump, etc., determine presence of material/mixture, determine volume/weight of material/mixture, etc.) and provide sensor controller 200 with the determined results. In some embodiments, the remote device is configured to perform only some of the functionality of sensor controller 200 and provide sensor controller 200 with the determined results for further processing. In some embodiments, sensor controller 200 is configured to both perform any of the functionality/methods described in greater detail below in addition to providing information received through communications interface 1632 to the remote device for processing. In this way, if sensor controller 200 is unable to communicably connect with the remote device (e.g., a remote server), sensor controller 200 is still configured to perform any of the functionality described in greater detail below. For example, if certain functionality of sensor controller 200 requires a large amount of processing power, the remote device may be configured to remotely perform the functionality of sensor controller 200 which requires the large amount of processing power and sensor controller 200 can be configured to perform the functions which do not require as high processing power. Specifically, sensor manager 1614 may be incorporated into a remote device (e.g., a remote server) and may wirelessly provide any of the results/determined values of sensor manager 1614 to sensor controller 200. Advantageously, this facilitates reducing processing requirements of sensor controller 200 by off-loading various functionality to a remote device.

Communications interface 1632 may be a network interface configured to facilitate electronic data communications between sensor controller 200 and various external systems or devices (e.g., wireless radio 1006, user interface device 1004, removable data storage device 1010, drum assembly controller 152, sensor assembly 190, first acceleration sensor 196, second acceleration sensor 198, a remote server, etc.). For example, sensor controller 200 may receive acceleration signals from sensor assembly 190 and output information/data regarding material properties present in mixer drum 102 via communications interface 1632. Sensor controller 200 may use communications interface 1632 to output results of the analyzed acceleration data/signals to user interface device 1004 and/or to store the results in results removable data storage device 1010.

Still referring to FIG. 16, processing circuit 1602 is shown to include a processor 1606 and memory 1604. Processor 1606 may be a general purpose or specific purpose processor, an application specific integrated circuit (ASIC), one or more field programmable gate arrays (FPGAs), a group of processing components, or other suitable processing components. Processor 1606 may be configured to execute computer code or instructions stored in memory 1604 or received from other computer readable media (e.g., CDROM, network storage, a remote server, etc.).

Memory 1604 may include one or more devices (e.g., memory units, memory devices, storage devices, etc.) for storing data and/or computer code for completing and/or facilitating the various processes described in the present disclosure. Memory 1604 may include random access memory (RAM), read-only memory (ROM), hard drive storage, temporary storage, non-volatile memory, flash memory, optical memory, or any other suitable memory for storing software objects and/or computer instructions. Memory 1604 may include database components, object code components, script components, or any other type of information structure for supporting the various activities and information structures described in the present disclosure. Memory 1604 may be communicably connected to processor 1606 via processing circuit 1602 and may include computer code for executing (e.g., by processor 1606) one or more processes described herein.

Referring still to FIG. 16, memory 1604 is shown to include a disturbance manager 1630, a baseline manager 1628, and a filter 1624, according to an exemplary embodiment. Disturbance manager 1630 receives acceleration signals from second acceleration sensor 198 (internal sensor signal), according to some embodiments. In some embodiments, the acceleration signals received from second acceleration sensor 198 are disturbed/noisy signals. Disturbance manager 1630 is configured to measure an amount of noise or disturbance present in acceleration signals received from second acceleration sensor 198 by comparing the acceleration signals from second acceleration sensor 198 to corresponding acceleration signals received from first acceleration sensor 196, according to some embodiments. In some embodiments, disturbance manager 1630 manager the acceleration signal received from first acceleration sensor 196 such that it can be compared to the acceleration signal received from second acceleration sensor 198. Disturbance manager 1630 may process or identify acceleration signals received from first acceleration sensor 196 and second acceleration sensor 198, and provide the processed acceleration signals to filter 1624 for filtering.

Filter 1624 is configured to filter noisy acceleration signals (e.g., acceleration signals received from second acceleration sensor 198) with respect to a clean (e.g., an undisturbed signal such as acceleration signals received from first acceleration sensor 196), according to some embodiments. For example, tangential acceleration signals received from second acceleration sensor 198 may be filtered with respect to tangential acceleration signals received from first acceleration sensor 196, radial acceleration signals received from second acceleration sensor 198 may be filtered with respect to radial acceleration signals received from first acceleration sensor 196, etc. In some embodiments, filter 1624 is a digital filter or an analog filter. In some embodiments, filter 1624 and/or disturbance manager 1630 facilitates identification of when signal noise occurs with respect to a radial acceleration signal received by first acceleration sensor 196 which can be used to determine mixer drum 102 orientation, speed, etc. For example, disturbance manager 1630 and filter 1624 can determine/identify when noise present in acceleration signals received from second acceleration sensor 198 exceed a predetermined threshold, deviate a predetermined percentage from the corresponding acceleration signals received from first acceleration sensor 196, deviate a standard deviation from the corresponding acceleration signals received from first acceleration sensor 196, etc. In some embodiments, filter 1624 and/or disturbance manager 1630 provide sensor manager 1614 with information regarding an amount of noise present in acceleration signals received from first acceleration sensor 196, and a corresponding undisturbed (e.g., corresponding acceleration signal received from first acceleration sensor 196) value, and/or a corresponding mixer drum 102 orientation, speed, etc. In some embodiments, disturbance manager 1630 is configured to use any of the techniques described in greater detail above with reference to FIGS. 11-14 to identify high-noise signals and corresponding mixer drum 102 orientations, speed, etc. In some embodiments, filter 1624 is a Fast Fourier Transform (FFT) filter.

Referring still to FIG. 16, sensor controller 200 includes a baseline manager 1628, according to some embodiments. In some embodiments, baseline manager 1628 is configured to generate a baseline series of information based on acceleration signals received from first acceleration sensor 196. For example, baseline manager 1628 may be configured to analyze the undisturbed acceleration signals received from first acceleration sensor 102, determine baseline acceleration series which characterize undisturbed acceleration signals, and provide the characteristic baseline acceleration series to sensor manager 1614. In some embodiments, baseline manager 1628 is configured to collect signals from second acceleration sensor 198, generate time-series data, and perform a sinusoidal curve fit to determine a characteristic equation of the undisturbed acceleration signals. In some embodiments, baseline manager 1628 collects information from first acceleration sensor 196 over a predetermined time period, and determines the characteristic behavior for the predetermined time period.

Referring still to FIG. 16, sensor controller 200 includes sensor manager 1614, according to some embodiments. In some embodiments, sensor manager 1614 receives mixer drum 102 properties (e.g., mixer drum radius, mixer drum volume, mixer drum shape, mixer drum weight, etc.) from mixer properties database 1608, identification functions/tables from identification database 1610 (e.g., functions, tables, algorithms, rules, conditions, etc., to identify various properties of the mixture present in mixer drum 102 based on acceleration signals), and historical data from data logging database 1612. In some embodiments, sensor manager 1614 is configured to store, write, or log determined information (e.g., material type, material slump, etc.) in data logging database 1612.

Sensor manager 1614 is configured to receive any of acceleration signals/data from first acceleration sensor 196, acceleration signals/data from second acceleration sensor 198, baseline/characteristic behaviors of acceleration signals from baseline manager 1628, noise amounts and corresponding acceleration signals from filter 1624 and/or disturbance manager 1630, according to some embodiments. In some embodiments, sensor manager 1614 uses these various information/data/signal inputs to determine any of whether water is present in mixer drum 102, a type of material present in mixer drum 102, an amount of material/mixture present in mixer drum 102, a slump of material/mixture present in mixer drum 102, a consistency of material/mixture present in mixer drum 102, material properties of the mixture/material present in mixer drum 102, entry/exit angles of the material/mixture present in mixer drum 102, available volume in mixer drum 102, weight of material/mixture present in mixer drum 102, speed of mixer drum 102, number of revolutions of mixer drum 102, orientation of mixer drum 102, etc. In some embodiments, sensor manager 1614 provides any of these to any of wireless radio 1006, user interface device 1004, removable data storage device 1006, data logging database 1612, etc.

Referring still to FIG. 16, sensor manager 1614 includes drum position manager 1616, speed manager 1618, and material manager 1620, according to some embodiments. In some embodiments, drum position manager 1616 is configured to determine any of a position/orientation of mixer drum 102, a number of revolutions of mixer drum 102, and material/mixture entry/exit angles. In some embodiments, speed manager 1618 is configured to determine any of an angular speed/velocity of mixer drum 102, a number of revolutions of drum mixer 102, and an angular acceleration of mixer drum 102. In some embodiments, material manager 1620 is configured to identify/determine various material properties of the material/mixture present in mixer drum 102, including but not limited to, material type, slump properties, amount of material present in mixer drum 102, consistency of mixture/material present in mixer drum 102, etc., or other material properties. The techniques and functionality of each of drum position manager 1616, speed manager 1618, material manager 1620, and more generally, sensor manager 1614 is described in greater detail below with reference to FIGS. 17-19, according to some embodiments.

Referring still to FIG. 16, sensor controller 200 includes verification manager 1622, according to some embodiments. In some embodiments, verification manager 1622 is configured to receive any of the information determined by sensor manager 1614 (e.g., amount of material present in mixer drum 102) to verify if the determined results of sensor manager 1614 are accurate. For example, in some embodiments, verification manager 1622 uses a concrete buildup algorithm to determine validity/accuracy of the available volume/material present as determined by sensor manager 1614 based on acceleration signals received from sensor assembly 190. In some embodiments, verification manager 1622 compares the remaining volume and/or amount of mixture present in mixer drum 102 as determined by sensor manager 1614 to the remaining volume/amount of mixture present in mixer drum 102 as determined according to the concrete buildup algorithm to determine accuracy of the remaining volume and/or amount of mixture present in mixer drum 102 as determined by sensor manager 1614. In some embodiments, an amount of buildup of material within mixer drum 102 displaces other material within mixer drum 102 and changes internal geometry of mixer drum 102. In some embodiments, based on differences between acceleration signals measured by first acceleration sensor 196 and second acceleration sensor 198, an amount of concrete buildup is detected.

Referring still to FIG. 16, memory 1604 includes communications manager 1626, according to some embodiments. In some embodiments, communications manager 1626 facilitates various communications protocols between sensor controller 200 and external devices/systems via communications interface 1632. In some embodiments, communications manager 1626 is configured to communicably connect sensor controller 200 with drum assembly controller 152. In some embodiments, communications manager 1626 is configured to determine commands to send to drum assembly controller 152 based on the results of sensor manager 1614 and/or verification results of verification manager 1622. In some embodiments, the commands sent to drum assembly controller 152 include commands to adjust an operation of mixer drum 102 in response to one or more conditions being met. In some embodiments, the commands sent to drum assembly controller 152 include instructions to automatically rotate mixer drum 102 to an orientation such that a solar panel positioned on an exterior surface of mixer drum 102 or on hatch portion 192 is at an optimal orientation (e.g., facing the sun) for charging. In some embodiments, any or all of the functionality of drum assembly controller 152 is incorporated into sensor controller 200 such that sensor controller 200 can directly adjust an operation of mixer drum 102. For example, communications manager 1626 may be configured to generate control signals for various controllable elements of concrete mixer truck 10 to adjust an operation of mixer drum 102 (e.g., orientation, speed, angular acceleration, etc.).

Figure 17:
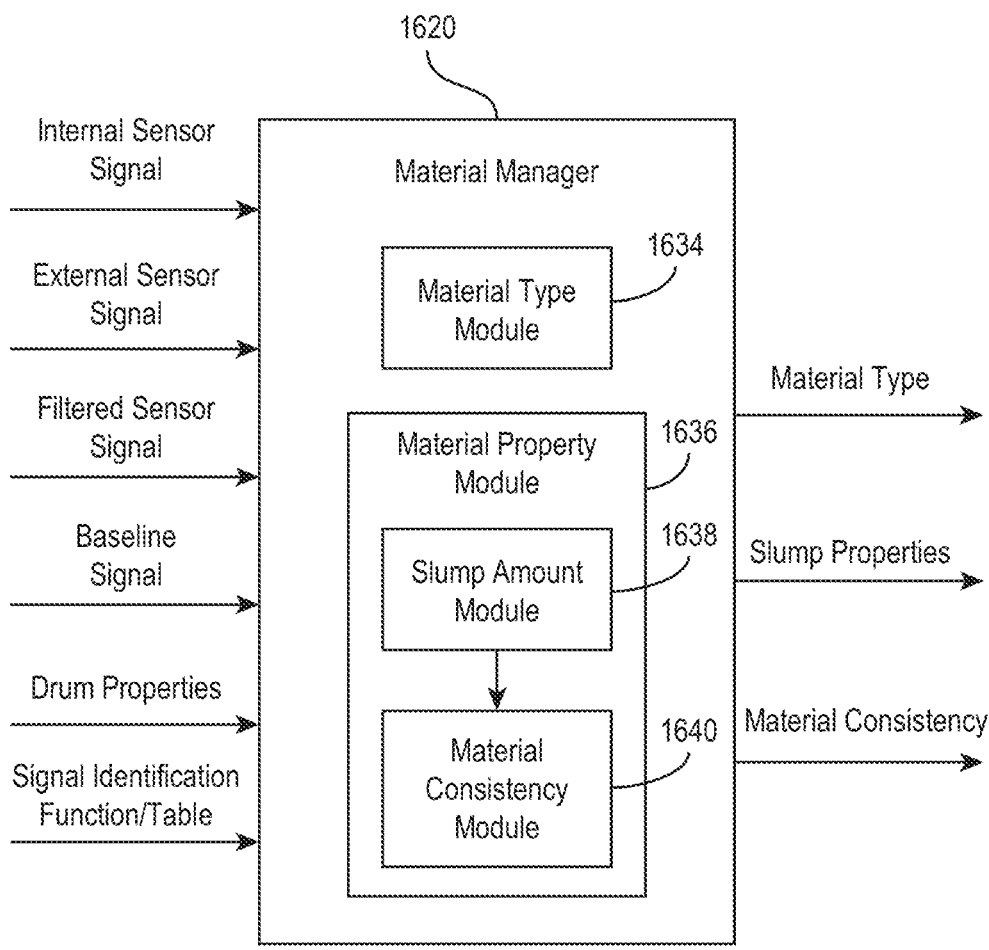
FIG. 17 is a block diagram of the material manager of the sensor controller of FIG. 10, according to an exemplary embodiment.

Referring now to FIG. 17, material manager 1620 is shown in greater detail, according to some embodiments. Material manager 1620 receives acceleration signals from both first acceleration sensor 196 and second acceleration sensor 198, filtered acceleration signals/data from filter 1624 and/or disturbance manager 1630, baseline/characteristic behavior of acceleration signals from baseline manager 1628, properties of mixer drum 102 from mixer properties database 1608, and one or more functions, tables, set of conditions, equations, etc., from identification database 1610 to identify various material/mixture properties based on the acceleration signals, according to some embodiments. In some embodiments, material manager 1620 outputs a type of material (e.g., water, concrete, rocks, empty, etc.) or an indication of material/mixture presence in mixer drum 102, slump of the material/mixture present in mixer drum 102, and general consistency of material/mixture present in mixer drum 102.

Referring still to FIG. 17, material manager 1620 is shown to include material type module 1634, according to some embodiments. In some embodiments, material type module 1634 is configured to determine if material/mixture is present in mixer drum 102, and if material/mixture is present in mixer drum 102, what type of material is in mixer drum 102. In some embodiments, material type module 1634 uses any of an equation, a function, a table, a set of conditions, a set of rules, etc., as provided by identification database 1610 to determine if mixture/material are present in mixer drum 102. In some embodiments, material type module 1634 uses any of the techniques described in greater detail above with reference to FIGS. 11-14 to determine if material/mixture is present in mixer drum 102. For example, material type module 1634 may monitor an amount of noise (e.g., a signal to noise ratio) of tangential acceleration signal, and if at any point along a revolution of mixer drum 102, the amount of noise exceeds a predetermined threshold value, material type module 1634 determines that material/mixture is present in mixer drum 102. In some embodiments, material type module 1634 compares the tangential acceleration signal as measured by second acceleration sensor 198 to the tangential acceleration signal as measured by first acceleration sensor 196 to determine if the amount of noise exceeds a predetermined threshold value or rapidly increases (e.g., spikes).

In some embodiments, material type module 1634 analyzes various properties (e.g., amount, frequency, at what point in the revolution of mixer drum 102 the noise occurs, etc.) of the noise in acceleration signals as measured by second acceleration sensor 198 to determine a type of material/mixture present in mixer drum 102. In some embodiments, material type module 1634 uses a relationship provided by identification database 1610 to determine a type of material/mixture present in mixer drum 102. In some embodiments, material type module 1634 receives an estimated slump, viscosity, or consistency from material property module 1636 to determine a type of material/mixture present in mixer drum 102.

Referring still to FIG. 17, material manager 1620 includes material property module 1636, according to some embodiments. In some embodiments, material property module 1636 is configured to determine various properties of the material/mixture present in mixer drum 102. In some embodiments, slump amount module 1638 of material property module 1636 uses a linear relationship provided by identification database 1610 to determine an amount of slump of the material/mixture present in mixer drum. In some embodiments, the linear relationship is defined as:

$$\frac{1}{S} = m \cdot M_{noise} + b$$

where S is a slump of the mixture (e.g., in millimeters), m is a slope constant determined empirically, $M_{noise}$ is a magnitude of noise (e.g., a signal to noise ratio) of a noisy acceleration signal (e.g., tangential acceleration signal as measured by second acceleration sensor 198) relative to an undisturbed/clean acceleration signal (e.g., a tangential acceleration signal as measured by first acceleration sensor 196), and b is an intercept constant determined empirically. In some embodiments, slump amount module 1638 uses a non-linear relationship defined as:

$$S = f_{slump}(M_{noise})$$

where $f_{slump}$ is an empirical relationship determined through testing. In some embodiments, $f_{slump}$ is a linear relationship, as shown above. In some embodiments, $f_{slump}$ is a non-linear relationship (e.g., exponential, polynomial, logarithmic, etc.). In some embodiments, slump amount module 1638 uses any of the techniques described in greater detail above with reference to FIG. 12 to determine slump of the material/mixture present in mixer drum 102. In some embodiments, slump amount module 1638 provides the determined slump of material/mixture in mixer drum 102 to material type module 1634 for use in determining a type of material/mixture present in mixer drum 102 and/or to determine if material/mixture is present in mixer drum 102. Advantageously, the determined slump of the material/mixture in mixer drum 102 can be used to determine if water should be added to the mixture. Additionally, knowing the slump of material/mixture in mixer drum 102 facilitates ensuring that an excessive amount of water is not added to the material/mixture which may decrease material/mixture strength after the mixture has cured.

Referring still to FIG. 17, material property module 1636 includes material consistency module 1640, according to some embodiments. In some embodiments, material consistency module 1640 is configured to qualitatively determine a consistency of the material/mixture present in mixer drum 102. For example, material consistency module 1640 may qualify the material/mixture present in mixer drum 102 as High Slump, Low Slump, Correct Slump. In some embodiments, material consistency module 1640 determines consistency which indicates whether water should be added or not using the criteria:

If $S_{min} < S < S_{max}$ Then "Correct Slump"

If $S > S_{max}$ Then "High Slump"

If $S < S_{min}$ Then "Low Slump"

These criteria can be used to determine a notification regarding a moisture/water content of the mixture. Material consistency module 1640 may output a consistency (e.g., Correct Slump, High Slump, Low Slump, etc.) and a recommended amount of water which must be added/removed to achieve "Correct Slump." In some embodiments, material consistency module 1640 uses a relationship between slump and water content to determine if water should be added/removed and a quantity of water which should be added/removed based on the slump of the mixture and the consistency of the mixture.

In some embodiments, material manager 1620 is configured to analyze the accelerations as measured by first acceleration sensor 196 and second acceleration sensor 198 to determine if a mixture (e.g., concrete) present in mixer drum 102 is homogenous. In some embodiments, material manager 1620 compares the accelerations measured by second acceleration sensor 198 to a reference acceleration signal typical of a homogenous mixture (e.g., homogenous concrete). In some embodiments, based on the differences between the acceleration as measured by second acceleration sensor 198 and the reference acceleration signal are used by material manager 1620 to determine a degree of homogeneity of the mixture present in mixer drum 102 or any other material properties of the mixture present in mixer drum 102. In some embodiments, material manager 1620 identifies various properties of the acceleration signal as provided by second acceleration sensor 198 to determine a degree of homogeneity of the mixture. For example, if an amount of noise of the acceleration signal as sensor assembly 190 passes through the mixture is relatively constant (although greater than the noise present when sensor assembly 190 is not passing through the mixture), material manager 1620 may determine that the mixture is homogenous, and therefore well-mixed. Advantageously, determining when the mixture is homogenous/well-mixed provides better insight. This insight can be used to cease rotating mixer drum 102 when the mixture/cement is homogenous/well-mixed, reducing the need for unnecessary revolutions, and increasing an efficiency of concrete mixer truck 10. Current standards on how much mixing is required (ASTM C94) require 70 revolutions for a "good" mix. Knowing when the concrete/mixture is sufficiently mixed could facilitate change of this requirement.

Referring now to FIG. 18, speed manager 1618 is shown in greater detail, according to some embodiments. Speed manager 1618 includes maximum acceleration module 1642, counter 1644, speed module 1646, and acceleration module 1648, according to some embodiments. In some embodiments, speed manager 1618 receives the same inputs as material manager 1620 and uses these inputs to determine angular velocity and angular acceleration of mixer drum 102 (outputs). Maximum acceleration module 1642 is configured to monitor acceleration (e.g., radial acceleration) as measured by first acceleration sensor 196, according to some embodiments. In some embodiments, maximum acceleration module 1642 compares a present acceleration value (e.g., $a_{r,present}$) to a previous acceleration value (e.g., $a_{r,previous}$). In some embodiments, if the present acceleration value is greater than the previous acceleration value, maximum acceleration module 1642 determines that the acceleration is increasing. Once the acceleration begins decreasing (e.g., $a_{r,present} < a_{r,previous}$), maximum acceleration module 1642 determines that the maximum acceleration has been reached, and causes counter 1644 to increase by a value of one. In some embodiments, maximum acceleration module 1642 determines if a maximum acceleration has occurred (e.g., maximum acceleration occurs when mixer drum 102 is in the orientation as shown in FIG. 7B or FIG. 7A for minimum acceleration) using the following criteria:

$$\text{If: } a(t - \Delta t) > a(t)$$
$$\text{and: } a(t - \Delta t) < a(t - 2\Delta t) \quad \text{Then: } a(t - \Delta t) = a_{max}$$

where a(t−Δt) is an acceleration value measured one time step Δt before a current acceleration value a(t), a(t−2Δt) is an acceleration value measured two time steps (2Δt) before the current acceleration value, $a_{max}$ is a maximum acceleration, and Δt is a time step (or sampling rate) at which the acceleration values are sampled. In some embodiments, maximum acceleration module 1642 does not determine that a maximum acceleration has occurred until a predetermined number of samples preceding and following the acceleration value in question (e.g., a(t−Δt)) are less than the acceleration value in question. In some embodiments, a predetermined number of samples preceding and following the acceleration value are averaged, and maximum acceleration module 1642 determines that a maximum acceleration has occurred if the acceleration value in question is greater than both the averages preceding and following the acceleration value in question. Finding a maximum acceleration value corresponds to determining a time at which point 1110 as shown in FIG. 13 occurs, according to some embodiments. In some embodiments, the maximum acceleration value and the time at which it occurs are stored and used to determine speed of mixer drum 102. In this way, maximum acceleration module may determine a set of maximum accelerations and the corresponding time values, shown as:

$a_{max,1} t_1$ $a_{max,2} t_2$ $a_{max} = a_{max,3} t_3$

. . . . . .

$a_{max,n} t_n$

Similarly, maximum acceleration module 1642 can determine occurrences of minimum acceleration. In some embodiments, maximum acceleration module 1642 uses any of the herein disclosed techniques to determine peaks and toughs (e.g., points 1110 and points 1116) of acceleration signals measured by first acceleration sensor 196. Using these maximum and/or minimum acceleration values and times at which they occur, period 1204 can be determined (see FIGS. 12-13).

Referring still to FIG. 18, maximum acceleration module 1642 increases counter 1644 by a value of one in response to a maximum acceleration value occurring. In some embodiments, counter 1644 can be used to keep a count of a number of revolutions of mixer drum 102. Advantageously, this facilitates determining if the mixture (e.g., concrete) has been sufficient mixed. For example, based on a number of completed revolutions of mixer drum 102, the homogeneity of the mixture can be determined. Some mixtures require 70 revolutions, while other mixtures may require more or less than 70 revolutions of mixer drum 102. Advantageously, knowing a number of completed revolutions of mixer drum 102 indicates knowing how many revolutions are yet to be completed before the mixture is sufficiently mixed. In some embodiments, the number of revolutions as counted by counter 1644 are used to determine how mixed the mixture is. In some embodiments, the number of revolutions as counted by counter 1644 are provided to speed module 1646 for use in determining angular speed of mixer drum 102.

Referring still to FIG. 18, speed manager 1618 includes speed module 1646, configured to determine an angular speed of mixer drum 102, according to some embodiments. In some embodiments, speed module 1646 receives a number of counts of maximum (or minimum) acceleration as measured by first acceleration sensor 196. In some embodiments, speed module 1646 determines an angular speed, co, based on acceleration signals received from first acceleration sensor 196. In some embodiment, speed module 1646 determines angular speed, co, based on the number of counts of the maximum acceleration and the times at which these maximum accelerations occur as provided by counter 1644 and/or maximum acceleration module 1642. In some embodiments, speed manager 1618 uses a number of counts over a time period as provided by counter 1644 and determines angular speed using the equation:

$$\omega_{avg} = \frac{n}{\Delta t_n}$$

where n is a number of revolutions (e.g., a number of maximum/minimum accelerations measured) over a time period $\Delta t_n$. In some embodiments, speed manager 1618 determines an angular speed between iteratively occurring maximum accelerations using the equation:

$$\omega_{avg} = \frac{1}{|t_1 - t_2|}$$

where $t_1$ and $t_2$ are times at which a maximum or minimum acceleration occurs (e.g., $a_{max,1}$ and $a_{max,2}$).

Referring still to FIG. 18, speed manager 1618 includes acceleration module 1648, according to some embodiments. In some embodiments, acceleration module 1648 is configured to determine an angular acceleration based on a change in angular speed as determined and provided by speed module 1646. For example, acceleration module 1648 may receive multiple angular speed values from speed module 1646 which represent angular speeds of mixer drum 102 at different times. In some embodiments, acceleration module 1648 uses the equation:

$$\alpha_{avg} = \frac{\Delta \omega}{\Delta t_\omega}$$

to determine an average angular acceleration.

In some embodiments, speed module 1646 is configured to determine a present angular speed based on the acceleration signals received from first acceleration sensor 196. Since as mixer drum 102 rotates, a portion of gravitational acceleration is measured by first acceleration sensor 196 in radial direction 204 and a portion of gravitational acceleration is measured by first acceleration sensor 196 in tangential direction 206, a relationship between radial acceleration (or tangential acceleration) and angular position (e.g., θ) can be determined, shown below:

$$\theta(t) = f_{\theta, a_r}(a_r(t))$$

where θ(t) is an angle at time t (see FIGS. 7A and 7B for definition of θ), $f_{\theta, a_r}$ is a function relating radial acceleration (e.g., as measured by first acceleration sensor 196) and $a_r(t)$ is radial acceleration at time t. In some embodiments, $f_{\theta,a_r}$ can be determined based on geometric principles and has the form:

$$\theta(t) = f_{\theta,a_r}(a_r(t)) = \sin^{-1}\left(\frac{a_r(t)}{g}\right)$$

Taking the time derivative of $f_{\theta,a_r}$ yields a present angular speed function ω, according to some embodiments. In some embodiments, speed module 1646 uses the angular speed function ω to determine a current angular speed of mixer drum 102. In some embodiments, the time derivative the angular speed function ω determines an angular acceleration function to determine a present angular acceleration α. It should be noted that these functions which speed module 1646 and/or acceleration module 1648 make the assumption that for first acceleration sensor 196, measured acceleration is largely due to gravity. In some embodiments, these function are determined by drum position manager 1616. In some embodiments, these functions are provided by identification database 1610.

Figure 19A:
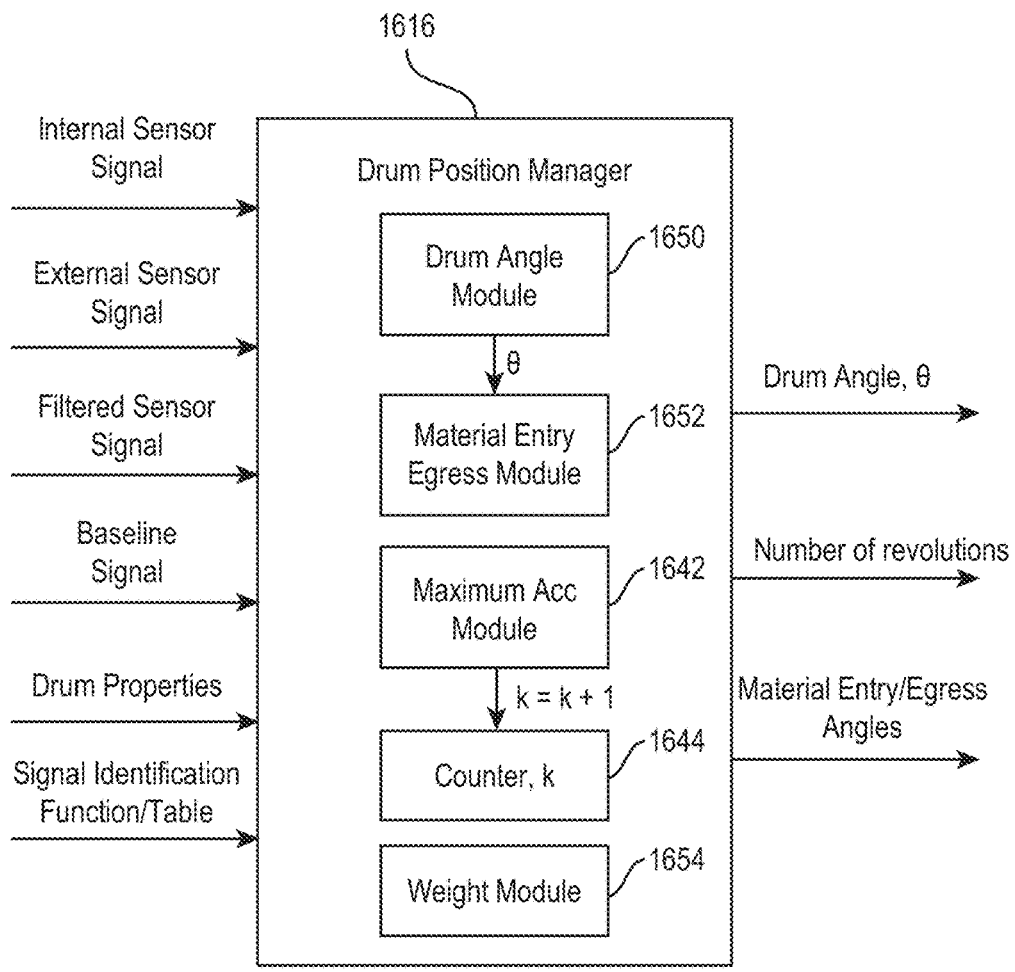
FIG. 19A is a block diagram of the drum position manager of the sensor controller of FIG. 10, shown to include a drum angle module, according to an exemplary embodiment.

Referring now to FIG. 19A, drum position manager 1616 is shown in greater detail, according to some embodiments. Drum position manager 1616 is configured to determine any of drum angle θ, a number of revolutions of mixer drum 102, and material/mixture entry/egress angles, according to some embodiments. In some embodiments, drum position manager 1616 includes drum angle module 1650, material entry/egress module 1652, maximum acceleration module 1642 and counter 1644, and weight module 1654. In some embodiments, drum position manager 1616 is configured to determine an orientation of mixer drum 102. In some embodiments, material entry/egress module 1652 is configured to determine an angle $\theta_1$ at which sensor assembly 190 first contacts material/mixture present in mixer drum 102, and an angle $\theta_2$ at which sensor assembly 190 ceases contacting (e.g., ceases passing through) material/mixture present in mixer drum 102. In some embodiments, material entry/egress module 1652 is configured to use various properties of mixer drum 102 to determine an amount, volume, weight, etc., of mixture/material present in mixer drum 102. In some embodiments, maximum acceleration module 1642 and counter 1644 are configured to determine a number of revolutions of mixer drum 102 over a time period, as described in greater detail above with reference to FIG. 18.

Figure 19B:
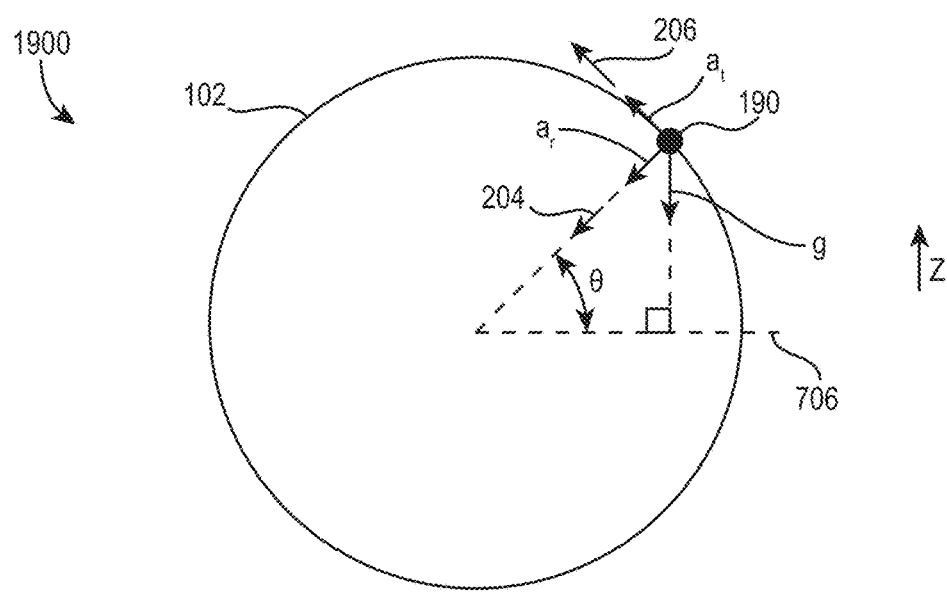
FIG. 19B is a diagram of a mixer drum and various accelerations used to determine an equation used by the drum angle module of FIG. 19A, according to an exemplary embodiment.

Drum angle module 1650 is configured to determine drum angle θ using an equation determined from diagram 1900 as shown in FIG. 19B, according to some embodiments. FIG. 19B illustrates mixer drum 102 rotated to an arbitrary orientation θ, according to some embodiments. As shown in FIG. 19B, θ is measured counter-clockwise from horizontal axis 706. Gravitational acceleration, g, always acts in the negative Z direction. Sensor assembly 190 measures radial acceleration α, in radial direction 204 and tangential acceleration $\alpha_t$ in tangential direction 206, according to some embodiments. In some embodiments, centripetal acceleration can be neglected, since gravitational acceleration g is much larger than the centripetal acceleration. From diagram 1900 as shown in FIG. 19B, it can be determined that sensor assembly 190 measures a portion of gravitational acceleration g in radial direction 204 and a portion of gravitational acceleration g in tangential direction 206, according to some embodiments. Using geometric principles, the amounts of gravitational acceleration measured by sensor assembly 190 (e.g., by first acceleration sensor 196) can be defined as:

$$a_r = g \cdot \sin(\theta)$$

$$a_t = g \cdot \cos(\theta)$$

From either of these equations, a function relating the orientation of mixer drum 102 based on either the radial acceleration measured by sensor assembly 190 or the tangential acceleration measured by sensor assembly 190:

$$\theta = \sin^{-1}\left(\frac{a_r}{g}\right)$$

$$\theta = \cos^{-1}\left(\frac{a_t}{g}\right)$$

In some embodiments, since tangential direction 206 is normal to radial direction 204 and since centripetal acceleration never acts in tangential direction 206, it is more accurate to use the inverse cosine equation to determine orientation θ of mixer drum 102.

Referring again to FIG. 19A, drum angle module 1650 may use either of the above equations to determine orientation of mixer drum 102 based on radial or tangential acceleration, according to some embodiments. In some embodiments, drum angle module 1650 uses the undisturbed/clean acceleration signals provided by first acceleration sensor 196. In some embodiments, drum angle module 1650 outputs present drum orientation to any of speed manager 1618, material manager 1620, verification manager 1622, communications manager 1626, data logging database 1612, and material entry/egress module 1652. In some embodiments, every time a particular drum orientation is reached (e.g., θ=0, θ=90, etc.), a counter is increased to keep track of a number of revolutions of drum mixer 102. In some embodiments, the number of revolutions is recorded over a time period and output for further use by sensor controller 200.

Referring still to FIG. 19A, drum position manager 1616 includes material entry/egress module 1652, according to some embodiments. In some embodiments, material entry/egress module 1652 monitors mixer drum orientation θ and determines $\theta_1$ and $\theta_2$ using any of the techniques described in greater detail above with reference to FIGS. 12-13. In some embodiments, material entry/egress module 1652 uses any of the techniques described in greater detail above with reference to FIGS. 12-13 to determine when an acceleration signal as measured by one of first acceleration sensor 196 or second acceleration sensor 198 (e.g., tangential acceleration as measured by second acceleration sensor 198) spikes (e.g., increases rapidly, indicating sensor assembly 190 has contacted material/mixture) and records drum orientation $\theta_1$ at this point. Similarly, when the noise of the acceleration signal decreases, indicating that sensor assembly 190 is no longer contacting/passing through material/mixture, drum angle module 1650 records drum orientation $\theta_2$, according to some embodiments.

In some embodiments, drum angle module 1650 uses $\theta_1$ and $\theta_2$ to determine an amount of material/mixture present in mixer drum 102. In some embodiments, drum angle module 1650 uses any of the techniques described in greater detail above with reference to FIG. 12. For example, drum angle module 1650 may use a relationship provided by identification database and/or mixer properties database 1608 to determine an amount of material/mixture present in mixer drum 102 based on $\theta_1$ and $\theta_2$. In some embodiments, the volume of material/mixture present in mixer drum 102 can be approximated by drum angle module 1650 using a function such as:

$$V_{mixture} = f_{volume}(\theta_1, \theta_2, r_{drum}, V_{drum})$$

where $V_{mixture}$ is a volume of mixture present in mixer drum 102, $r_{drum}$ is a radius of mixer drum 102, and $V_{drum}$ is a volume of mixer drum 102. In some embodiments, function $f_{volume}$ is determined using empirical data. In some embodiments, function $f_{volume}$ is determined based on geometric relationships of mixer drum 102. In some embodiments, function $f_{volume}$ is provided by identification database 1610. In some embodiments, the various mixer drum 102 properties used in function $f_{volume}$ are provided by mixer properties database 1608.

In some embodiments, a weight of material/mixture present in mixer drum 102 is determined by weight module 1654 based on the volume determined by drum angle module 1650. In some embodiments, weight module 1654 is configured to perform any of the techniques/functionality of drum angle module 1650 as described above to determine an estimated volume of material/mixture present in mixer drum 102. In some embodiments, weight module 1654 uses the estimated volume to determine the weight of the material/mixture present in mixer drum 102 using the following equation:

$$w_{mixture} = \rho_{mixture} V_{mixture} g$$

where $w_{mixture}$ is a weight of the mixture present in mixer drum 102, $\rho_{mixture}$ is a density of the mixture present in mixer drum 102, $V_{mixture}$ is the estimated volume of the mixture present in mixer drum 102, and g is acceleration due to gravity. In some embodiments, weight module 1654 determines an estimated density of the mixture based on slump as determined by material manager 1620. In some embodiments, weight module 1654 uses a relationship shown below:

$$\rho_{mixture} = f_{density}(S_{mixture})$$

to determine estimated density of the mixture, where $S_{mixture}$ is slump of the mixture present in mixer drum 102 as determined by material manager 1620, and $f_{density}$ is a relationship (e.g., an empirical relationship).

The estimated weight of the mixture can be advantageously used for a variety of applications. For example, in some embodiments, the estimated/calculated weight of the mixture can be used to automate axle pressure. Advantageously, using acceleration sensors (e.g., first acceleration sensor 196 and second acceleration sensor 198) is more cost effective than using scales as other systems do. Additionally, using the system as described in the present disclosure to estimate weight/payload of mixture/concrete in mixer drum 102 completely removes a need for an expensive scale system.

Referring again to FIG. 16, sensor controller 200 is shown outputting any of the information determined by sensor manager 1614 to user interface device 1004. In some embodiments, user interface device 1004 is configured to display to a user any of the information described hereinabove. In some embodiment, user interface device 1004 is positioned within cab 14 of concrete mixer truck 10 to facilitate notifying the user regarding the various information/data. In some embodiments, the information/data is provided to the user in forms including but not limited to, values, alerts, graphs, time series data, etc. In some embodiments, sensor controller 200 is configured to generate control signals to adjust an operation of mixer drum 102. In some embodiments, user interface device 1004 includes one or more levers, buttons, switches, etc., configured to receive an input and adjust an operation of mixer drum 102 based on the received input. In some embodiments, user interface device 1004 is configured to display graphs showing the accelerations measured by first acceleration sensor 196 and second acceleration sensor 198. In some embodiments, user interface device 1004 is configured to display FFT results of the accelerations measured by first acceleration sensor 196 and second acceleration sensor 198. In some embodiments, removable storage device 1006 is configured to store any of the data/information received, analyzed, output, etc. and determined by sensor controller 200. Advantageously, this allows removable data storage device 1006 to be easily removed so that the data stored on removable data storage device 1006 can be analyzed by a different controller (e.g., a computer).

Figure 21:
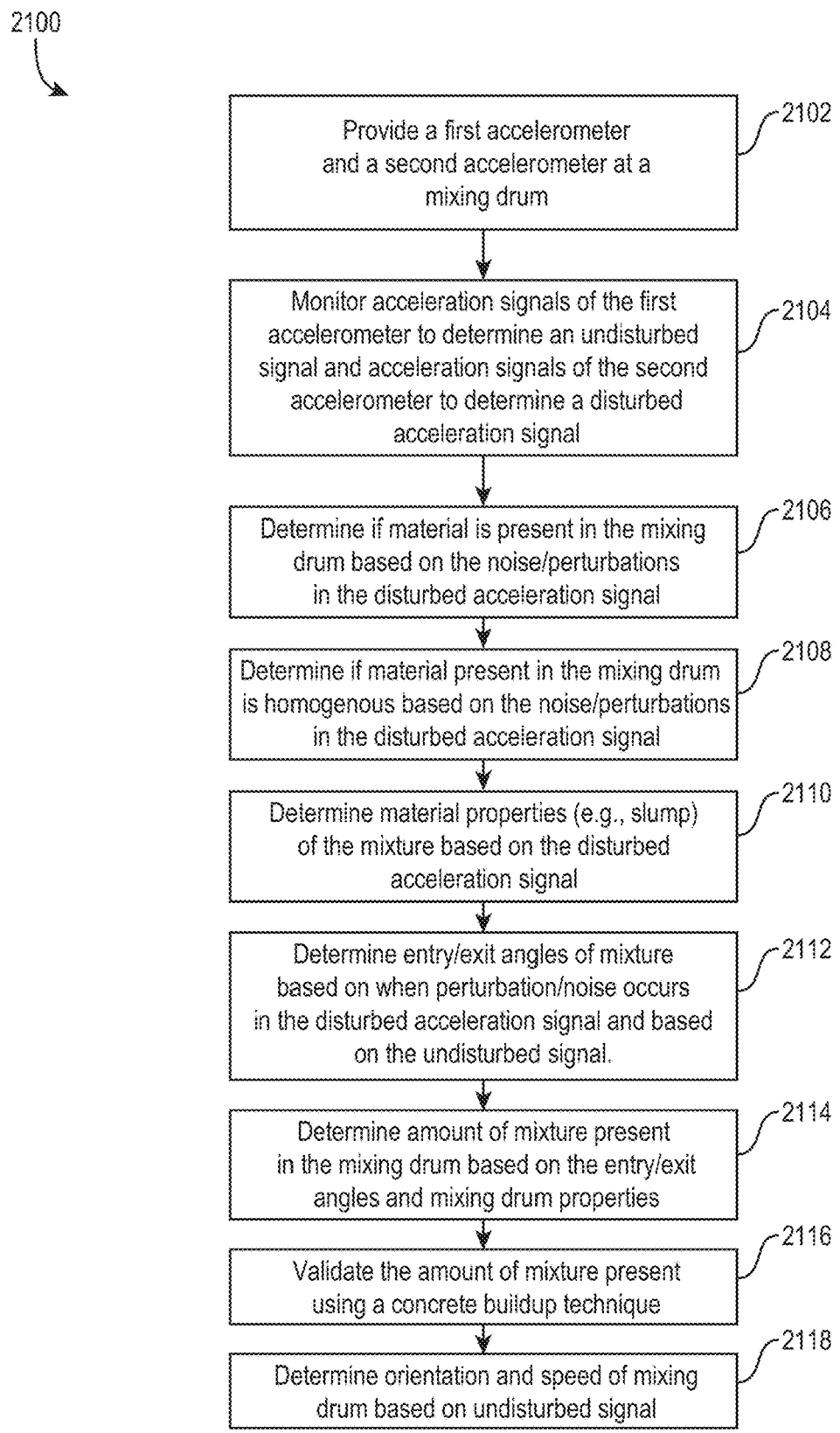
FIG. 21 is a process for measuring and analyzing acceleration information of a concrete mixing drum, according to an exemplary embodiment.

Referring now to FIG. 21, a process 2100 for analyzing accelerometer signals is shown, according to an exemplary embodiment. Process 2100 illustrates the various functions of sensor controller 200 as a process, and should be understood in the context of the techniques described throughout the present application. Process 2100 includes steps 2102-2118 and can be performed by sensor controller 200 with sensor assembly 190.

Process 2100 includes providing a first accelerometer and a second accelerometer at a mixing or mixer drum (step 2102), according to an exemplary embodiment. Step 2102 can be achieved by installing sensor assembly 190 on mixer drum 102 so that first acceleration sensor 196 is outside of mixer drum 102 and second acceleration sensor 198 is inside of mixer drum 102. In some embodiments, first acceleration sensor 196 is positioned such that it measures/produces undisturbed acceleration signals. In some embodiments, first acceleration sensor 196 is positioned within an enclosure. In some embodiments, first acceleration sensor 196 is positioned within sensor assembly 190 (e.g., within protrusion 194).

Process 2100 includes monitoring acceleration signals of the first accelerometer to determine an undisturbed signal and monitoring acceleration signals of the second accelerometer to determine a disturbed acceleration signal (step 2104). Step 2104 can be achieved by receiving sensory measurements from first acceleration sensor 196 and second acceleration sensor 198 at sensor controller 200. In some embodiments, the first accelerometer is not affected by mixture or material within the mixing drum and is therefore undisturbed. In some embodiments, the second accelerometer is positioned within the mixing drum so that the second accelerometer fluctuates or generates the disturbed acceleration signal as it passes through the mixture or material in the drum.

Process 2100 includes determining if material is present in the mixing drum based on the noise/perturbations in the disturbed acceleration signals (step 2106). Step 2106 may be performed by sensor controller 200, or more specifically by material manager 1620. Step 2106 includes monitoring noise/perturbations present in the acceleration signals received from second acceleration sensor 198 to determine if material is present in mixer drum 102. In some embodiments, if an amount of noise in the disturbed signal exceeds a predetermined threshold value, then it is determined that material is present. In some embodiments, step 2106 includes monitoring radial acceleration as measured by second acceleration sensor 198 and comparing this radial acceleration to radial acceleration as measured by first acceleration sensor 196 to determine an amount of noise present in the radial acceleration as measured by second acceleration sensor 198. In this way, the undisturbed acceleration signals may serve as a baseline which can be used in comparison to the disturbed acceleration signals. In some embodiments, step 2106 includes determining if material is present in mixer drum 102 based on an amount of noise present in the radial acceleration signal as measured by second acceleration sensor 198.

Process 2100 includes determining if material present in the mixing drum is homogenous based on the noise/perturbation in the disturbed acceleration signal(s) (step 2108). Step 2108 may include identifying a characteristic of the disturbed acceleration signal which indicates that the mixture/material present in the mixing drum is homogenous. In some embodiments, step 2108 is performed by sensor controller 200.

Process 2100 includes determining material properties (slump) of the mixture based on the disturbed acceleration signal (step 2110). Step 2110 may include monitoring an amount of noise present in the disturbed acceleration signal and using the amount of noise and a relationship to determine an estimated slump of the mixture. In some embodiments, step 2110 is performed by sensor controller 200.

Process 2100 includes determining entry/exit angles of mixture based on when perturbations/noise occurs in the disturbed acceleration signal and based on the undisturbed acceleration signal (step 2112). Step 2112 may include monitoring the disturbed acceleration signal, and determining areas of increased noise. The areas of increased noise may be indicative of the probe (sensor assembly 190) passing through mixture present in the mixing drum. Step 2112 may include determining angles (e.g., angular orientation of the mixing drum) where the increased noise begins and ends based on the undisturbed acceleration signal. Step 2112 may be performed by sensor controller 200.

Process 2100 includes determining an amount of mixture present in the mixing drum based on the entry/exit angles and mixing drum properties (or mixing drum type) (step 2114). Step 2114 may include estimating a volume of the mixture present based on the entry/exit angles and the mixing drum properties/type. Step 2114 may include estimating a density of the mixture present based on the estimated slump and a relationship between slump and density. Step 2114 may include estimating a weight of mixture present based on the entry/exit angles and the mixing drum properties/type or based on the estimated volume and the estimated density of the mixture present in the mixing drum. Step 2114 may be performed by sensor controller 200.

Process 2100 includes validating the amount of mixture present using a concrete buildup technique (step 2116). Step 2116 may include comparing the results of step 2114 to the results of the concrete buildup technique to determine if the results of step 2114 are accurate. Step 2116 may include comparing the results of step 2114 to any other method of estimating an amount of mixture present in the mixing drum.

Process 2100 includes determining orientation and speed of the mixing drum based on the undisturbed signal (step 2118). Step 2118 may include using a relationship between either of measured radial acceleration or measured tangential acceleration and orientation of the mixing drum. Step 2118 may include using the measured radial or measured tangential acceleration and determining the orientation of the mixing drum based on the measured radial or measured tangential acceleration. In some embodiment, step 2118 is performed by drum position manager 1616 and/or speed manager 1618.

The present disclosure contemplates methods, systems and program products on memory or other machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products or memory comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, by way of example, instructions and data which cause a general purpose computer, special purpose computer, or special purpose processing machines to perform a certain function or group of functions.

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the figures. It should be noted that the orientation of various elements may differ according to other exemplary embodiments, and that such variations are intended to be encompassed by the present disclosure.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

It is important to note that the construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claims.

The invention claimed is:

1. A mixer vehicle comprising:
   a mixer drum;
   a first accelerometer and a second accelerometer, wherein the first accelerometer is configured to produce baseline acceleration signals and the second accelerometer is configured to measure accelerations within the mixer drum to produce disturbed acceleration signals; and
   a controller configured to:
      obtain the baseline acceleration signals and the disturbed acceleration signals from the first accelerometer and the second accelerometer as the mixer drum rotates;
      determine an amount of noise in the disturbed acceleration signals relative to the baseline acceleration signals based on a comparison between the baseline acceleration signals and the disturbed acceleration signals; and
      use the amount of noise in the disturbed acceleration signals to determine a presence of material and one or more properties of the material within the mixer drum.

2. The mixer vehicle of claim 1, wherein the one or more properties include a degree of homogeneity of the material, a slump of the material, and a consistency of the material.

3. The mixer vehicle of claim 2, wherein the controller is further configured to:
   determine the slump of the material based on an amount of noise in the disturbed acceleration signals using an empirical relationship that defines slump of the material as a function of the amount of noise; and
   use the consistency of the material to determine whether water should be added to or removed from the material.

4. The mixer vehicle of claim 1, wherein using the amount of noise in the disturbed acceleration signals to determine the presence of the material comprises determining the presence of material based on a signal to noise ratio of the disturbed acceleration signals.

5. The mixer vehicle of claim 1, wherein the controller is further configured to determine an entry angle and an exit angle of the material within the mixer drum based on the baseline acceleration signals and the disturbed acceleration signals.

6. The mixer vehicle of claim 5, wherein the controller is further configured to determine any of a volume, and a weight based on the entry angle and the exit angle of the material.

7. The mixer vehicle of claim 6, wherein the controller is further configured to validate the weight of the material within the mixer drum by comparing the weight determined based on the entry angle and the exit angle of the material to a weight determined by a concrete buildup algorithm.

8. The mixer vehicle of claim 6, wherein the controller is further configured to use the weight of the material to adjust an operation of one or more systems or devices of the mixer vehicle.

9. The mixer vehicle of claim 1, wherein the second accelerometer is positioned inside of the mixer drum and passes through the material as the mixer drum rotates, the second accelerometer producing the disturbed acceleration signals as a result of passing through the material; and
   wherein the first accelerometer is positioned outside of the mixer drum.

10. The mixer vehicle of claim 1, wherein the controller is further configured to determine at least one of an orientation and an angular speed of the mixer drum based on at least one of the baseline acceleration signals and the disturbed acceleration signals.

11. The mixer vehicle of claim 10, wherein the controller is further configured to automatically adjust an orientation of the mixer drum based on the orientation such that a solar panel disposed on the mixer drum points in an upwards direction.

12. The mixer vehicle of claim 1, wherein the first accelerometer and the second accelerometer are positioned on a probe, wherein the probe comprises a urethane cover.

13. A sensing system for a concrete mixer vehicle, the sensing system comprising a processing circuit configured to:
   obtain baseline acceleration signals from a first accelerometer and disturbed acceleration signals from a second accelerometer, wherein the second accelerometer is positioned within a mixer drum of the concrete mixer vehicle and produces the disturbed acceleration signals;
   determine an amount of noise in the disturbed acceleration signals relative to the baseline acceleration signals based on a comparison between the baseline acceleration signals and the disturbed acceleration signals; and
   use the amount of noise in the disturbed acceleration signals to determine a presence of material and one or more properties of the material within the mixer drum.

14. The sensing system of claim 13, wherein the one or more properties include a degree of homogeneity of the material, a slump of the material, and a consistency of the material.

15. The sensing system of claim 14, wherein the processing circuit is further configured to:
   determine the slump of the material based on an amount of noise in the disturbed acceleration signals using an empirical relationship that defines a slump of the material as a function of the amount of noise; and
   use the consistency of the material to determine whether water should be added to or removed from the material.

16. The sensing system of claim 13, wherein using the amount of noise in the disturbed acceleration signals to determine the presence of the material comprises determining the presence of material based on a signal to noise ratio of the disturbed acceleration signals.

17. The sensing system of claim 13, wherein the processing circuit is further configured to determine:
   an entry angle and an exit angle of the material within the mixer drum based on the baseline acceleration signals and the disturbed acceleration signals; and
   any of a volume or a weight based on the entry angle and the exit angle of the material within the mixer drum.

18. The sensing system of claim 13, wherein the second accelerometer is positioned inside of the mixer drum and passes through the material as the mixer drum rotates, the second accelerometer producing the disturbed acceleration signals as a result of passing through the material; and wherein the first accelerometer is positioned outside of the mixer drum.

19. A method for determining a slump of a material within a concrete mixer drum, the method comprising:
   providing a first accelerometer and a second accelerometer on a probe that extends into the concrete mixer drum, wherein the first accelerometer is disposed outside of the concrete mixer drum and is configured to produce baseline acceleration signals as the concrete mixer drum rotates, and the second accelerometer is disposed within the concrete mixer drum on the probe and is configured to produce disturbed acceleration signals as the concrete mixer drum rotates and the probe passes through the material;
   determining an indication of an amount of noise in the disturbed acceleration signals based on a comparison of the baseline acceleration signals and the disturbed acceleration signals; and
   using the amount of noise in the disturbed acceleration signals to estimate the slump of the material within the concrete mixer drum.

20. The method of claim 19, further comprising:
   adjusting an operation of the concrete mixer drum using the slump of the material within the concrete mixer drum.

* * * * *